United States Patent [19]

Ueda et al.

[11] Patent Number: 5,126,361
[45] Date of Patent: Jun. 30, 1992

[54] IMIDAZOLE DERIVATIVES AND USE THEREOF

[75] Inventors: Tohru Ueda; Akira Matsuda; Noriaki Minakawa, all of Sapporo; Takuma Sasaki, Kanazawa; Yoshikazu Yanagi, Kawanishi, all of Japan

[73] Assignee: Yamasa Shoyu Kabushiki Kaisha, Chiba, Japan

[21] Appl. No.: 702,210

[22] Filed: May 15, 1991

Related U.S. Application Data

[62] Division of Ser. No. 316,969, Sep. 28, 1989, Pat. No. 5,059,590.

[30] Foreign Application Priority Data

Feb. 29, 1988 [JP] Japan .................................. 63-46921
Apr. 1, 1988 [JP] Japan .................................. 63-82089
Apr. 1, 1988 [JP] Japan .................................. 63-82090

[51] Int. Cl.$^5$ .................... A61K 31/415; C07D 233/90
[52] U.S. Cl. ....................................... 514/400; 548/343
[58] Field of Search .......................... 548/343; 514/400

[56] References Cited

U.S. PATENT DOCUMENTS 4,924,000  5/1990  Hesse et al. ........................ 548/343

FOREIGN PATENT DOCUMENTS 0306868  3/1989  European Pat. Off. .
2-225471  9/1990  Japan .

Primary Examiner—Patricia L. Morris
Assistant Examiner—Lenora Miltenberger
Attorney, Agent, or Firm—Wenderoth, Lind & Ponack

[57] ABSTRACT

Disclosed are imidazole derivatives represented by formula [I]:

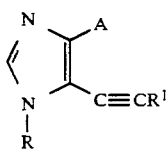

wherein R is a hydrogen atom or

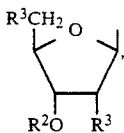

wherein $R^2$ is a hydrogen atom or a hydroxy protecting group, $R^2$ protecting either a single hydroxy or two hydroxies together when $R^2$ is a hydroxy protecting group, and $R^3$ is a hydrogen atom or $OR^2$; A is $CONH_2$ or CN; and $R^1$ is a hydrogen atom, lower alkyl, hydroxy lower alkyl, or phenyl.

Also disclosed are six processes for producing these novel compounds among which a typical process comprises reacting a starting imidazole compound having a halogen at the 5-position thereof with an acetylene derivative to alkynylate the 5-position.

Furthermore, the compounds have remarkable antitumor activities and therefore can provide novel antitumor agents.

2 Claims, No Drawings

IMIDAZOLE DERIVATIVES AND USE THEREOF

This is a Rule 60 Divisional of Ser. No. 07/316,969 filed Sep. 28, 1989, now U.S. pat. No. 5,059,590.

BACKGROUND OF THE INVENTION

The present invention relates to imidazole derivatives, a process for the production thereof, and antitumor agents comprising the imide-zole derivatives as active ingredients.

There is little difference between tumor cells and normal cells in respect of physiological properties. For this reason, antitumor agents so far provided for clinical applications tend to produce more serious side effects if the antitumor activities thereof are higher and thus cannot always attain satisfactory therapeutic effects. Under such situation, an enhanced therapeutic effect on tumors can be obtained only by a proper combination of chemotherapy with a surgical treatment or radiotherapy.

As indicated above, antitumor agents so far provided for clinical applications are accompanied by problems in respect of therapeutic effects and side effects and thus are not most acceptable.

A primary object of the present invention is to provide novel compounds having remarkable antitumor activities.

SUMMARY OF THE INVENTION

As a result of extensive research efforts for the production of novel compounds expected to have antitumor activities, we have successfully synthesized novel imidazole derivatives represented by the following formulae [I] and [IIg].

More particularly, the present invention relates to imidazole derivatives represented by formula [I]:

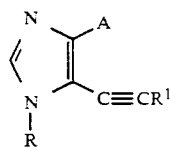

[I]

wherein R is a hydrogen atom or

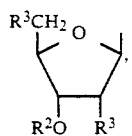

wherein $R^2$ is a hydrogen atom or a hydroxy protecting group, $R^2$ protecting either a single hydroxy or two hydroxides together when $R^2$ is a hydroxy protecting group, and $R^3$ is a hydrogen atom or $OR^2$; A is $CONH_2$ or $CN$; and $R^1$ is a hydrogen atom, lower alkyl, hydroxy lower alkyl, or phenyl.

This invention also relates to imidazole derivatives represented by formula [IIg]:

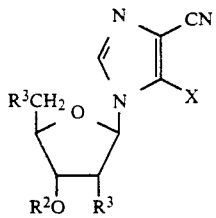

[IIg]

wherein X is a halogen atom, and $R^2$ and $R^3$ are as defined above.

The present invention further relates to a process for producing imidazole derivatives represented by formula [Ic]:

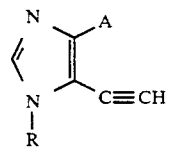

[Ic]

wherein R and A are as defined above,
which process (hereinafter referred to as "Process I") comprises the following Steps (1) and (2)

(1) reacting a compound of formula [IIc] with an ethynyltin compound to obtain a compound of formula IIIc]:

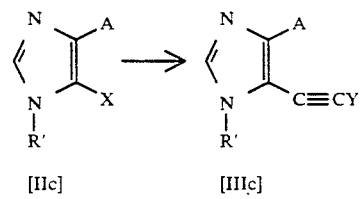

[IIc]   [IIIc]

wherein R' is a hydrogen atom or

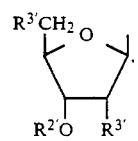

wherein $R^{2'}$ is a hydroxy protect group, $R^{2'}$ protecting either a single hydroxy or two hydroxies together, and $R^{3'}$ is a hydrogen atom or $OR^{2'}$; A and X are as defined hereinbefore; and Y is silyl; and (2) removing the silyl represented by Y in the compound of formula [IIIc] and, as needed, removing the hydroxy protecting group represented by $R^{2'}$ to obtain the compound of formula [Ic]

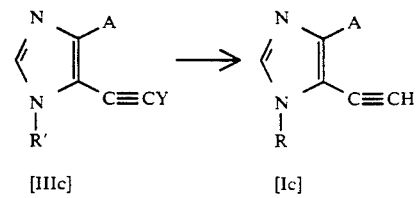

[IIIc]   [Ic]

wherein R', R, A and Y are as defined above

The present invention still further relates to a process for producing imidazole derivatives represented by formula [Id]:

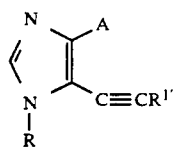 [Id]

wherein A and R are as defined above, and R¹' is lower alkyl, hydroxy lower alkyl, or phenyl, which process (hereinafter referred to as "Process II") comprises: reacting a starting compound of formula [IId]:

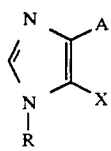 [IId]

wherein A, R and X are as defined above, with an acetylene derivative of formula [V]:

 [V]

wherein R¹ is as defined above, and, when R is a protected ribose, 2-deoxyribose or 5-deoxyribose, removing, as needed, the hydroxy protecting group represented by R² to obtain the imidazole derivative of formula [Id].

Furthermore, we have found that, by using as a starting compound a carbonitrile compound (formula [If]- shown below) which is an imidazole derivative of formula [I]having cyano (—CN) at the 4-position, a carboxamide compound (formula [Ie]shown below) having carbamoyl (—CONH₂) at the 4-position can be synthesized easily.

It is generally known that, when a carbonitrile compound is subjected to hydrolysis, the cyano (—CN) is hydrolyzed to once form carbamoyl (—CONH₂), which is further hydrolyzed to form carboxyl (—COOH). We, however, have found that, by subjecting a carbonitrile compound of the following formula [If]to hydrolysis, a carboxamide compound of the following formula [Ie]can be produced with high efficiency and substantially no carboxylate compounds are formed.

Thus, the present invention relates to a process for producing imidazole derivatives represented by formula [Ie]:

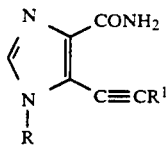 [Ie]

wherein R and R¹ are as defined above, which process (hereinafter referred to as "Process III") comprises: subjecting a starting imidazole derivative of formula [If]:

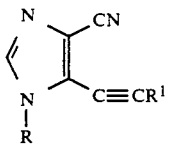 [If]

wherein R and R¹ are as defined above, to hydrolysis to obtain the imidazole derivative of formula [Ie].

The present invention, in another aspect thereof, relates to a process for producing imidazole derivatives represented by formula [Ih]:

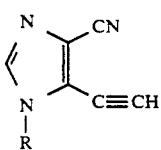 [Ih]

wherein R is as defined above, which process (hereinafter referred to as "Process IV") comprises: reacting a starting compound of formula [IIh]:

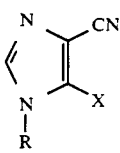 [IIh]

wherein R and X are as defined above, with an acetylene derivative of formula [Vh]:

 [Vh]

wherein Y is as defined previously, and then removing the silyl, and, when R is a protected ribose, 2-deoxyribose or 5-deoxyribose, optionally removing the hydroxy protecting group represented by R² to obtain the imidazole derivative of formula [Ih].

The present invention, in still another aspect thereof, relates to a process for producing imidazole derivatives represented by formula [Ib]:

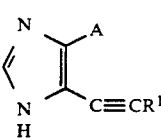 [Ib]

wherein A and R¹ are as defined above, which process (hereinafter referred to as "Process V") comprises: subjecting a starting imidazole derivative of formula [Ia]:

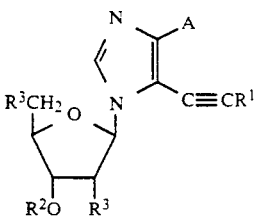

wherein A, $R^1$, $R^2$ and $R^3$ are as defined above, to cleavage of the glycosidic bond to obtain the imidazole derivative of formula [Ib].

Furthermore, the present invention relates to a process for producing imidazole derivatives represented by formula [Ii]:

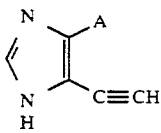

wherein A is as defined above, which process (hereinafter referred to as "Process VI") comprises:
subjecting a starting imidazole derivative of formula [IIIi]:

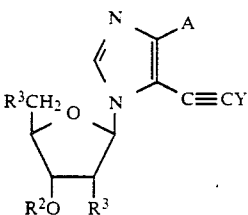

wherein A, $R^2$, $R^3$ and Y are as defined above, to hydrolysis to remove the silyl while inducing cleavage of the glycosidic bond thereby to obtain the imidazole derivative of formula [Ii].

The present invention, in a further aspect thereof, relates to an antitumor agent comprising an effective amount of an imidazole derivative of the above shown formula [I] and a pharmaceutically acceptable carrier or adjuvant.

The present invention, in still further aspect thereof, relates to a method for the treatment of tumors in a subject (including a human) which comprises administering to said subject, a therapeutically effective amount of the antitumor agent described above.

DETAILED DESCRIPTION OF THE INVENTION

Hereinafter, the present invention will be set forth in detail.

Compound of the present invention

The compounds of the present invention are represented by formula [I] shown hereinbefore. Examples of the lower alkyl represented by $R^1$ in formula [I] are straight- or branched-chain alkyls having, preferably not more than 10, and more preferably not more than 4, carbon atoms. Preferred from the antitumor activity viewpoint set forth later are straight- or branched-chain alkyls such as methyl, ethyl, propyl, isopropyl, isobutyl, butyl, and t-butyl.

Exemplary hydroxy lower alkyls represented by $R^1$ are staight- or branched-chain alkyls having, preferably, not more than 10 carbon atoms which are substituted with one or more hydroxies at any position(s). Preferred from the antitumor activity as in the case of the lower alkyl mentioned above are hydroxy lower alkyls with 1 to 4 carbon atoms which are substituted with one or more hydroxies at any position(s) such as hydroxymethyl, α-hydroxyethyl, β-hydroxyethyl, α,β-dihydroxyethyl, α-hydroxypropyl, β-hydroxypropyl, γ-hydroxypropyl, α,β-dihydroxypropyl, α,γ-dihydroxypropyl, β,γ-dihydroxypropyl, α-hydroxymethylethyl, β-hydroxymethylethyl, α,β-dihydroxymethylethyl, α-hydroxybutyl, β-hydroxybutyl, γ-hydroxybutyl, δ-hydroxybutyl, α,β-dihydroxybutyl, α,γ-dihydroxybutyl, α,δ-dihydroxybutyl, α,β,γ-trihydroxybutyl, and β,γ,δ-trihydroxybutyl.

The hydroxy protecting group represented by $R^2$ or $R^{2'}$ may be any of those customarily used as hydroxy protecting groups for nucleosides, for example, acyls such as acetyl, chloroacetyl, dichloroacetyl, trifluoroacetyl, methoxyacetyl, propionyl, n-butyryl, (E)-2-methyl-2-butenoyl, isobutyryl, pentanoyl, benzoyl, o-(dibromomethyl)benzoyl, o-(methoxycarbonyl)benzoyl, p-phenyl-benzoyl, 2,4,6-trimethylbenzoyl, p-toluoyl, p-anisoyl, p-chlorobenzoyl, p-nitrobenzoyl, and α-naphthoyl; alkyloxymethyls such as methoxymethyl, ethoxymethyl, and n-propoxymethyl; substituted ethyls such as 1-ethoxyethyl and 1-methyl-1-methoxyethyl; aralkyls such as benzyl, phenetyl, 3-phenylpropyl, p-methoxybenzyl, p-nitrobenzyl, p-halobenzyl, p-cyanobenzyl, diphenylmethyl, triphenylmethyl, α- or β-naphthylmethyl, and α-naphthyldiphenylmethyl; pyranyls such as tetrahydropyran-2-yl and 4-methoxytetrahydropyran-4-yl; silyls such as trimethylsilyl, triethylsilyl, isopropyldimethylsilyl, t-butyldimethylsilyl, methyldi-t-butylsilyl triisopropylsilyl, and tetraisopropyldisiloxanyl (TIPDS); acetal- or ketal-type protecting groups such as ethylidene, propylidene, isopropylidene, benzylidene, cyclohexylidene, cyclopentylidene, methoxymethylidene, ethoxymethylidene, and dimethoxymethylidene; alkyloxycarbonyls such as methoxycarbonyl, ethoxycarbonyl, and t-butoxycarbonyl; and phosphoryls such as $-PO(OH)_2$ and $>PO(OH)$.

It should be noted, however, that the hydroxy protecting group may protect either a single hydroxy or two hydroxies together.

In the latter case, the protecting group can protect the 2'- and 3'-positions or 3'- and 5'-positions in the sugar moiety at the same time.

Examples of such protecting group are acetal- or ketal-type protecting groups, phosphoryls and TIPDS.

The compound of formula [I] wherein R is a ribose, 2-deoxyribose or 5-deoxyribose, or a derivative thereof having one or more protecting groups at any hydroxy position(s) of the formula:

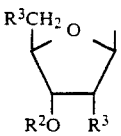

is represented by formula [Ia]:

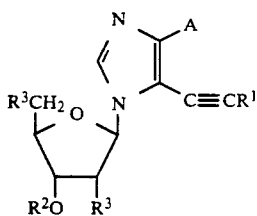

wherein A, $R^1$, $R^2$ and $R^3$ are as defined above.

Typical examples of the compound of formula [Ia]-wherein A is carbamoyl ($CONH_2$) include ribonucleosides such as 5-(phenylethyn-1-yl)-1-$\beta$-D-ribofuranosylimidazole-4-carboxamide, 5-ethynyl-1-$\beta$-D-ribofuranosylimidazole-4-carboxamide, 5-(1-propyn-1-yl)-1-$\beta$-D-ribofuranosylimidazole-4-carboxamide, 5-(1-butyn-1-yl)-1-$\beta$-D-ribofuranosylimidazole-4-carboxamide, 5-(1-pentyn-1-yl)-1-$\beta$-D-ribofuranosylimidazole-4-carboxamide, 5-(1-hexyn-1-yl)-1-$\beta$-D-ribofuranosylimidazole-4-carboxamide, 5-(heptyn-1-yl)-1-$\beta$-D-ribofuranosylimidazole-4-carboxamide, 5-(1-octyn-1-yl)-1-yl)-1-$\beta$-D-ribofuranosylimidazole-4-carboxamide, 5-(1-nonyn-1-yl)-1-$\beta$-D-ribofuranosylimidazole-4-carboxamide, 5-(1-decyn-1-yl)-1-$\beta$-D-ribofuranosylimidazole-4-carboxamide, 5-(1-undecyn-1-yl)-1-$\beta$-D-ribofuranosylimidazole-4-carboxamide, 5-(1-dodecyn-1-yl)-1-$\beta$-D-ribofuranosylimidazole-4-carboxamide, 5-(3-methyl-1-butyn-1-yl)-1-$\beta$-D-ribofuranosylimidazole-4-carboxamide, 5-(3,3-dimethyl-1-propyn-1-yl)-1-$\beta$-D-ribofuranosylimidazole-4-carboxamide, 5-(3-methyl-1-pentyn-1-yl)-1-$\beta$-D-ribofuranosylimidazole-4-carboxamide, 5-(4-methyl-1-pentyn-1-yl)-1-$\beta$-D-ribofuranosylimidazole-4-carboxamide, 5-(3-hydroxy-1-propyn-1-yl)-1-$\beta$-D-ribofuranosylimidazole-4-carboxamide, 5-(3-hydroxy-1-butyn-1-yl)-1-$\beta$-D-ribofuranosylimidazole-4-carboxamide, 5-(4-hydroxy-1-butyn-1-yl)-1-$\beta$-D-ribofuranosylimidazole-4-carboxamide, 5-(3,4-dihydroxy-1-butyn-1-yl)-1-$\beta$-D-4-carboxamide ribofuranosylimidazole-4-carboxamide, 5-(3-hydroxy-1-pentyn-1-yl)-1-$\beta$-D-ribofuranosylimidazole-4-carboxamide, 5-(4-hydroxy-1-pentyn-1-yl)-1-$\beta$-D-ribofuranosylimidazole-4-carboxamide, 5-(5-hydroxy-1-pentyn-1-yl)-1-$\beta$-D-ribofuranosylimidazole-4-carboxamide, 5-(3,4-dihydroxy-1-pentyn-1-yl)-1-$\beta$-D-ribofuranosylimidazole-4-carboxamide, 5-(4,5-dihydroxy-1-pentyn-1-yl)-1-$\beta$-D-ribofuranosylimidazole-4-carboxamide, 5-(4-hydroxy-3-methyl-1-butyn-1-yl)-1-$\beta$-D-ribofuranosylimidazole-4-carboxamide, 5-(6-hydroxy-1-hexyn-1-yl)-1-$\beta$-D-ribofuranosylimidazole-4-carboxamide, 5-(4-hydroxy-1-hexyn-1-yl)-1-$\beta$-D-ribofuranosylimidazole-4-carboxamide, and 5-(3-methyl-5-hydroxy-1-penten-1-yl)-1-$\beta$-D-ribofuranosylimidazole-4-carboxamide, or deoxyribonucleosides which are designated similarly as the above enumerated compounds except that the "$\beta$-D-ribofuranosyl" is replaced by "(2-deoxy-$\beta$-D-ribofuranosyl) or "(5-deoxy-$\beta$-D-ribofuranosyl)"; and compounds having hydroxies in the sugar moiety thereof protected with the aforementioned protecting groups.

Typical examples of the compound of formula [Ia]-wherein A is cyano (CN) are ribonucleosides such as 5-(phenylethyn-1-yl)-1-$\beta$-D-ribofuranosylimidazole-4-carbonitrile, 5-ethynyl-1-$\beta$-D-ribofuranosylimidazole-4-carbonitrile, 5-(1-propyn-1-yl)-1-$\beta$-D-ribofuranosylimidazole-4-carbonitrile, 5-(1-butyn-1-yl)-1-$\beta$-D-ribofuranosylimidazole-4-carbonitrile, 5-(1-pentyn-1-yl)-1-$\beta$-D-ribofuranosylimidazole-4-carbonitrile, 5-(1-hexyn-1-yl)-1-$\beta$-D-ribofuranosylimidazole-4-carbonitrile, 5-(1-heptyn-1-yl)-1-$\beta$-D-ribofuranosylimidazole-4-carbonitrile, 5-(1-octyn-1-yl)-1-$\beta$-D-ribofuranosylimidazole-4-carbonitrile, 5-(1-nonyn-1-yl)-1-$\beta$-D-ribofuranosylimidazole-4-carbonitrile, 5-(1-decyn-1-yl)-1-$\beta$-D-ribofuranosylimidazole-4-carbonitrile, 5-(1-undecyn-1-yl)-1-$\beta$-D-ribofuranosylimidazole-4-carbonitrile, 5-(1-dodecyn-1-yl)-1-$\beta$-D-ribofuranosylimidazole-4-carbonitrile, 5-(3-methyl-1-butyn-1-yl)-1-$\beta$-D-ribofuranosylimidazole-4-carbonitrile, 5-(3,3-dimethyl-1-propyn-1-yl)-1-$\beta$-D-ribofuranosylimidazole-4-carbonitrile, 5-(3-methyl-1-pentyn-1-yl)-1-$\beta$-D-ribofuranosylimidazole-4-carbonitrile, 5-(4-methyl-1-pentyn-1-yl)-1-$\beta$-D-ribofuranosylimidazole-4-carbonitrile, 5-(3-hydroxy-1-propyn-1-yl)-1-$\beta$-D-ribofuranosylimidazole-4-carbonitrile, 5-(3-hydroxy-1-butyn-1-yl)-1-$\beta$-D-ribofuranosylimidazole-4-carbonitrile, 5-(4-hydroxy-1-butyn-1-yl)-1-$\beta$-D-ribofuranosylimidazole-4-carbonitrile, 5-(3,4-dihydroxy-1-butyn-1-yl)-1-$\beta$-D-ribofuranosylimidazole-4-carbonitrile, 5-(3-hydroxy-1-pentyn-1-yl)-1-$\beta$-D-ribofuranosylimidazole-4-carbonitrile, 5-(4-hydroxy-1-pentyn-1-yl)-1-$\beta$-D-ribofuranosylimidazole-4-carbonitrile, 5-(5-hydroxy-1-pentyn-1-yl)-1-$\beta$-D-ribofuranosylimidazole-4-carbonitrile, 5-(3,4-dihydroxy-1-pentyn-1-yl)-1-$\beta$-D-ribofuranosylimidazole-4-carbonitrile, 5-(4,5-dihydroxy-1-pentyn-1-yl)-1-$\beta$-D-ribofuranosylimidazole-4-carbonitrile, 5-(4-hydroxy-3-methyl-1-butyn-1-yl)-1-$\beta$-D-ribofuranosylimidazole-4-carbonitrile, 5-(6-hydroxy-1-hexyn-1-yl)-1-$\beta$-D-ribofuranosylimidazole-4-carbonitrile, 5-(4-hydroxy-1-hexyn-1-yl)-1-$\beta$-D-ribofuranosylimidazole-4-carbonitrile, and 5-(3-methyl-5-hydroxy-1-pentyn-1-yl)-1-$\beta$-D-ribofuranosylimidazole-4-carbonitrile, or deoxyribonucleosides which are designated similarly as the above enumerated compounds except that the "$\beta$-D-ribofuranosyl" is replaced by "(2-deoxy-$\beta$-D-ribofuranosyl)" or "(5-deoxy-$\beta$-D-ribofuranosyl)"; and compounds having hydroxies in the sugar moiety thereof protected with the aforementioned protecting groups.

The compounds of the present invention represented by formula [I]also include the above indicated nucleosides having 1 to 3 phosphoryl groups introduced on the hydroxies at the 2'-, 3'- and 5'-positions thereof.

Such compounds can be obtained by organosynthetically or enzymatically phosphorylating nucleosides according to a conventional method. The organic synthesis includes phosphorylation of nucleosides with phosphorus oxychloride in the presence of trialkylphosphoric acid and phosphorylation of nucleosides with 2-cyanoethyl phosphate using dicyclohexylcarbodiimide as a condensing agent.

The compound of formula [I] wherein R is hydrogen is represented by formula [Ib]:

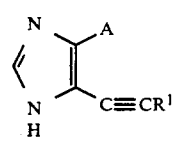

wherein A and $R^1$ are as defined above.

Examples of the compound of formula [Ib] wherein A is carbamoyl (CONH₂) are 5-(phenylethyn-1-yl)imidazole-4-carboxamide when $R^1$ is phenyl, 5-ethynylimidazole-4-carboxamide when $R^1$ is a hydrogen atom, 5-(lower alkyl-substituted ethyn-1-yl)imidazole-4-carboxamide when $R^1$ is lower alkyl, and 5-(hydroxy lower alkyl-substituted ethyn-1-yl)imidazole-4-carboxamide when $R^1$ is hydroxy lower alkyl, the lower alkyl being any of those mentioned hereinbefore as examples of $R^1$.

Examples of the compound of formula [Ib] wherein A is cyano (CN) are 5-(phenylethyn-1-yl)imidazole-4-carbonitrile when $R^1$ is phenyl, 5-ethynylimidazole-4-carbonitrile when $R^1$ is a hydrogen atom, 5-(lower alkyl-substituted ethyn-1-yl)imidazole-4-carbonitrile when $R^1$ is lower alkyl, and 5-(hydroxy lower alkyl-substituted ethyn-1-yl)imidazole-4-carbonitrile when $R^1$ is hydroxy lower alkyl, the lower alkyl being any of the those mentioned hereinbefore as examples of $R^1$.

Another compound of the present invention is represented by formula [IIg] shown hereinbefore. Examples of the halogen atom represented by X in formula [IIg] are iodine, bromine and chlorine, iodine and bromine being preferred. Examples of the hydroxy protecting group represented by $R^2$ in formula [IIg] are the same as those in formula [I] mentioned previously.

Typical examples of the compound of formula [IIg] are ribonucleosides such as 5-halogeno-1-β-D-ribofuranosylimidazole-4-carbonitrile, for example, 5-iodo-1-β-D-ribofuranosylimidazole-4-carbonitrile, and 5-bromo-1-β-D-ribofuranosylimidazole-4-carbonitrile, or deoxyribonucleosides which are designated similarly as the above enumerated compounds except that the "β-D-ribofuranosyl" is replaced by "(2-deoxy-β-D-ribofuranosyl)" or "(5-deoxy-β-D-ribofuranosyl)", and compounds having hydroxies in the sugar moiety thereof protected with the aforementioned protecting groups.

Production of the compounds of the present invention

The processes according to the present invention will now be described individually in detail.

Preparation of the starting compounds:

The compound of formula [IIc] used as a starting compound in Process I can be prepared by halogenating the 5-position of the imidazole ring in a compound of formula [VI]:

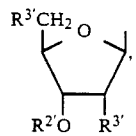
[VI]

wherein A and R' are as defined above.

The halogenation of the compound of formula [VI] is a halogenation reaction through a diazonium compound and can be carried out, for example, in accordance with the Nair and Richardson method (J. Org. Chem., 45, 3969–3974(1980)).

Exemplary halogenating agents useful herein are tribromomethane for bromination and diiodomethane for iodination, and these halogenating agents also serve as reaction solvents. The halogenation reaction can be accomplished by dissolving the compound of formula [VI] and 2- to 30-fold mols of an alkyl nitrite (e.g., isoamyl nitrite or butyl nitrite) per mol of the compound in a halogenating agent and causing reaction for 10 minutes to hours at 50° C. to the solvent reflux temperature.

The compound of formula [IIc] thus prepared can be isolated and purified by a suitable combination of isolation and purification methods customarily applied to nucleic acid compounds (e.g., various chromatographic procedures such as adsorption and ion exchange, and recrystallization).

When the compound of formula [VI] is the nucleoside having protecting groups in the sugar moiety thereof, i.e., wherein R' is

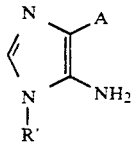

the compound can be produced by introducing protecting groups represented by $R^{2'}$ on the hydroxies in the sugar moiety of the corresponding unprotected nucleoside (derivatives such as 1-β-D-ribofuranoside, 1-(2-deoxy-β-D-ribofuranoside) or 1-(5-deoxy-β-D-ribofuranoside) of 5-aminoimidazole-4-carboxamide or 5-aminoimidazole-4-carbonitrile).

The introduction of the protecting groups on the hydroxies in the sugar moiety of the unprotected nucleoside may be conducted in accordance with a method ordinarily employed for the particular protecting groups selected.

For example, an acyl group can be introduced by causing reaction in the presence of 3- to 15-fold mols of an acylating agent- (an acid anhydride or acid chloride of the acid corresponding to $R^{2'}$) per mol of the unprotected nucleoside in a solvent (e.g., a basic solvent such as pyridine, picoline, diethylaniline, tributylamine, and triethylamine or a mixture thereof with acetonitrile, dimethylformamide, dimethylacetamide, formamide, chloroform, dichloromethane, dioxane, tetrahydrofuran or dimethylaminopyridine) at a temperature of from 0 to 50° C. for 1 to 30 hours.

The compound of formula [IId], i.e., a starting compound in Process II, wherein R is

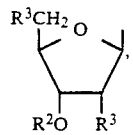

equivalent to the above compound of formula [IIc] from which the hydroxy protecting groups in the sugar moiety are optinally removed.

The removal of the hydroxy protecting groups in the sugar moiety may be carried out in accordance with a method ordinarily employed for the particular protecting groups selected. For example, acyls, when used as the hydroxy protecting groups, can be removed by alkaline hydrolysis utilizing methanol-ammonia (methanolic ammonia), conc. ammonia water and the like.

The compound of formula [IIh], i.e., a starting compound in Process IV, is equivalent to the above-mentioned compound of formula [IIc] wherein A is cyano (CN) and the hydroxy protecting groups represented by $R^{2'}$ (when the compound is a nucleoside) are optionally removed.

Process I:

Process I according to the present invention comprises two reaction steps, i.e., Step (1) of reacting the compound of formula [IIc] prepared as above with an ethynyltin compound, and Step (2) of removing the silyl and, as needed, removing the hydroxy protecting group.

Step (1):

The ethynyltin compound especially suitable for use in Step (1) is represented by formula [IV]:

$$YC\equiv CSnZ_3 \qquad [IV]$$

wherein Y is silyl and Z is lower alkyl.

Examples of the silyl represented by Y in the formula are trimethylsilyl, t-butyldimethylsilyl, methyldi-t-butylsilyl, and triisopropylsilyl.

Specific examples of the lower alkyl represented by Z are alkyls having 1 to 4 carbon atoms such as methyl, ethyl, propyl and butyl.

Such ethynyltin compounds can be prepared by the Stille and Simpson method (J. Am. Chem. Soc., 109, 2138-2152(1987)). For example, silylated acetylene (e.g., (trimethylsilyl)acetylene) and butyl lithium are dissolved in an ether solvent such as tetrahydrofuran, and the resulting solution is reacted with a halogenated trialkyltin (e.g., trimethyltin chloride, tributyltin chloride and trimethyltin bromide), whereby the desired ethynyltin compound of formula [IV] can be obtained.

Step (1) in Process I involves reacting the above described ethynyltin compound with the starting compound of the above shown formula [IIc] in a solvent (e.g., N,N-dimethylformamide, N,N-dimethylacetamide, dimethylsulfoxide, acetonitrile, tetrahydrofuran and dioxane) to obtain the compound.. of formula [IIIc]mentioned hereinbefore.

This reaction proceeds efficiently in the presence of a palladium catalyst. Exemplary palladium catalysts are bis(acetonitrile)palladium dichloride, bis(triphenylphosphine)palladium dichloride, bis(benzonitrile)palladium dichloride, a nd tetrakis(triphenylphosphine)palladium.

The Step (1) reaction can be carried out with 1- to 2-fold mols of ah ethynyltin compound per mol of the compound of formula [IIc] and a catalytic amount of a palladium catalyst at a temperature of from 0 to 200° C., preferably from 50 to 150° C., for 1 to 30 hours.

The compound of formula [IIIc] thus obtained is isolated and purified, as needed, by isolation and purification methods commonly applied to nucleic acid compounds (e.g., various chromatographic procedures such as adsorption and ion exchange, and recrystallization), and subjected to the following Step (2).

Step (2):

Step (2) is the reaction step of removing the silyl in the compound of formula [IIIc] and, as needed, removing the hydroxy protecting group represented by $R^{2'}$ to obtain the compound of formula [Ic].

The removal of the silyl may be carried out by a conventional method, for example, acidic hydrolysis using hydrochloric acid-tetrahydrofuran-water, alkaline hydrolysis using methanol-ammonia, or ammonium fluoride treatment.

In the case where R' is a ribose, 2-deoxyribose or 5-deoxyribose in which hydroxies are protected, the removal of hydroxy protecting groups represented by $R^{2'}$ may also be accomplished in accordance with a method customarily employed for the particular protecting groups selected. For instance, acyls, when used as the hydroxy protecting groups, can be removed by alkaline hydrolysis using methanol-ammonia, conc. ammonia water and the like.

The compound of formula [Ic] thus obtained can be isolated and purified by isolation and purification methods ordinarily applied to nucleic acid compounds (e.g., various chromatographic procedures such as adsorption and ion exchange, and recrystallization).

Process II:

Process II comprises reacting the aforementioned starting compound of formula [IId] with an acetylene derivative of formula [V]:

$$HC\equiv CR^{1'} \qquad [V]$$

wherein $R^{1'}$ is as defined above, and optionally removing the hydroxy protecting group represented by $R^2$ to obtain the compound of formula [Id].

The acetylene derivative of formula [V] used in the reaction may be selected from those having the corresponding $R^{1'}$ depending on the species of the compound of formula [Id]. When $R^{1'}$ is lower alkyl or hydroxy lower alkyl, examples thereof are similar to those exemplified for $R^1$.

For the solvent, a basic solvent such as triethylamine, tributylamine, trioctylamine, N,N,N',N'-tetramethyl-1,8-naphthalenediamine, dimethylaniline, diethylaniline and pyridine or a mixture thereof with acetonitrile, N,N-dimethylformamide, dimethyl sulfoxide, N,N-dimethylacetamide, tetrahydrofuran or dioxane can be employed.

The reaction in Process II proceeds efficiently in the presence of a palladium catalyst similarly as in Process I. Examples of the palladium catalyst are the same as were set forth in Process I.

The reaction can be conducted with 1- to 3-fold mols, preferably 1- to 2-fold mols, of an acetylene derivative per mol of the compound of formula [IId] in the presence of a catalytic amount of a palladium catalyst at a temperature of from 50 to 150° C., preferably from 90 to 110° C., for 1 to 30 hours.

When the compound of formula [Id] thus obtained is a nucleoside, the hydroxy protecting group represented by $R^2$ is removed, as needed.

The removal of the protecting group may be carried out in accordance with a method customarily used for the particular protecting group selected. For example, acyl, when used as $R^2$, can be removed by alkaline hydrolysis using methanol-ammonia, conc. ammonia water and the like.

The compound of formula [Id] can be isolated and purified by isolation and purification methods usually employed for nucleic acid compounds (e.g., various chromatographic procedures such as adsorption and ion exchange, and recrystallization).

Process III:

Process III comprises subjecting the compound of formula [If] to hydrolysis to convert the cyano(—CN) at the 4-position of the imidazole ring therein into carbamoyl(—CONH$_2$).

The starting compound of formula [If] wherein $R^1$ is lower alkyl, hydroxy lower alkyl or phenyl is equivalent to the compound of formula [Id] obtained by the preceding Process II wherein A is cyano (CN).

Thus, the compound of formula [If] can be prepared by Process II which comprises reacting the starting compound of formula [IIh]:

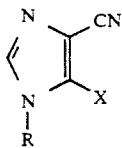

wherein R and X are as defined earlier, i.e., the compound of formula [IId] wherein A is CN, with the above shown acetylene derivative of formula [V].

The starting compound of formula [If] wherein $R^1$ is hydrogen is represented by formula [Ih] shown earlier, and can be prepared by Process IV set forth hereinlater.

The hydrolysis in Process III may be any of those which are employed in the preparation of carboxamide derivatives from nitrile derivatives, for example, acidic, neutral or alkaline hydrolysis. Preferred is neutral or alkaline hydrolysis, and more preferred is alkaline hydrolysis.

More specifically, alkaline hydrolysis can be accomplished by reacting the compound of formula [If] with hydrogen peroxide in the presence of a base such as sodium hydroxide, potassium hydroxide or ammonium hydroxide (ammonia water) at a temperature of from 10 to 50° C., preferably at room temperature, for 1 to 10 hours.

The solvent may be any of those which dissolve the starting compound and the desired end product and yet do not hinder the reaction, for example, an alcoholic solvent such as methanol or ethanol.

The compound of formula [Ie] thus obtained can be isolated and purified by a suitable combination of conventional isolation and purification methods for nucleic acid compounds (e.g., various chromatographic procedures such as adsorption and ion exchange, and recrystallization).

The compound of formula [Ie] can be easily and efficiently prepared by subjecting the compound of formula [If] to hydrolysis according to Process III, whereby even 5-ethynylimidazole-4-carboxamide of formula [Ie] wherein $R^1$ is hydrogen can be prepared by an extremely simple procedure without using an ethynyltin compound as in Process I.

Process IV:

Process IV comprises reacting the starting compound of formula [IIh] with the silylated acetylene derivative of formula [Vh]:

 [Vh]

to synthesize a compound of formula [Ih']:

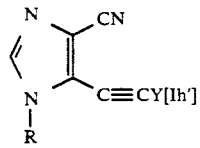

wherein R and Y are as defined earlier, and removing the silyl from the compound, and, when R is a protected ribose, 2-deoxyribose or 5-deoxyribose residue, optionally removing the hydroxy protecting group represented by $R^2$ to obtain the desired compound of formula [Ih] shown hereinbefore.

Examples of the silyl Y in the compound of formula [Vh] are silyls previously enumerated for the compound of formula [IV].

The reaction for the preparation of the compound of formula [Ih'] from the compounds of formulae [IIh] and [Vh] can be carried out in the same solvent in the presence of the same catalyst under the same reaction conditions as in Process II.

The reaction for the removal of the silyl from the compound of formula [Ih'] synthesized by the above reaction may be conducted in accordance with a conventional method, for example, acidic hydrolysis using hydrochloric acid-tetrahydrofuran-water, alkaline hydrolysis utilizing methanol-ammonia, or ammonium fluoride treatment.

In the case where R is a ribose, 2-deoxyribose or 5-deoxyribose, in which hydroxies are protected, the removal of hydroxy protecting groups represented by $R^2$ can be accomplished similarly in accordance with the method described in Process II.

The compound of formula [Ih] thus obtained can be isolated and purified by conventional isolation and purification methods for nucleic acid compounds (e.g., various chromatographic procedures such as adsorption and ion exchange, and recrystallization).

Process V:

Process V comprises subjecting the starting compound of formula [Ia] to cleavage of the glycosidic bond to obtain the compound of formula [Ib].

Basically, a reaction ordinarily conducted for cleavage of the glycosidic bond in nucleosides may be applied with modifications required depending upon the species of the starting compound and the desired product compound. For example, the reaction may be carried out in accordance with a conventional hydrolysis method under acidic conditions. More specifically, the reaction can be accomplished by allowing the starting compound to react in water or a water-containing solvent in the presence of an inorganic acid such as hydrochloric acid, sulfuric acid and hydrobromic acid or an organic acid such as methanesulfonic acid and p-toluenesulfonic acid at 50° C. to the reflux temperature for several tens of minutes to several tens of hours, preferably 1 to 5 hours.

In view of the solubility of the starting compound and the product compound, a suitable solvent such as alcohols, e.g., methanol, ethanol and propanol, or ethers, e.g., dioxane, tetrahydrofuran and diethyl ether, may be added to the reaction solution in order to dissolve the compounds.

After completion of the reaction, the compound of formula [Ib] can be isolated and purified by a suitable combination of isolation and purification methods customarily applied to nucleic acid-type bases (e.g., various chromatographic procedures such as adsorption and ion exchange, and recrystallization).

Process VI:

Process VI comprises subjecting the starting compound of formula [IIIi] to hydrolysis to remove the silyl while inducing cleavage of the glycosidic bond thereby to obtain the compound of formula [Ii].

Basically, the reaction can be carried out by the same method under the same reaction conditions as in the hydrolysis reaction described in Process V above.

In view of the solubility of the starting compound and the product compound, especially in view of the fact that the starting compound having silyl is sparingly soluble in water, a suitable solvent such as alcohols and ethers exemplified in Process V may be added to the reaction solution in order to dissolve the compounds After completion of the reaction, the compound of formula [Ii] can be isolated and purified by a suitable combination of conventional isolation and purification methods for nucleic acid-type bases (e.g., various chromatographic procedures such as adsorption and ion exchange, and recrystallization).

Utility of the compound of the present invention

The compounds of the present invention represented by formula [I] have antitumor activity, and the drugs comprising these compounds as an active ingredient are used clinically for the treatment of tumors.

While the dose level of the compound of formula [I]incorporated in the drugs of the present invention as an active ingredient may vary depending, for example, upon the species of the compound, the severity of patients' diseases and their tolerance for the drugs, and should be determined ultimately by doctors, 0.1 to 10 g per day of the compound is ordinarily administered to an adult in one portion or several portions The drugs can be administered in any mode suited for the route of administration.

The drugs of the present invention can be prepared for administration by any conventional method suitable for the purpose. Thus, the drugs include pharmaceutical compositions containing imidazole derivatives of formula [I] suitable as medicines for humans.

Such compositions are provided for administration by a conventional method through any pharmaceutically acceptable carriers or adjuvants required.

In the case, for example, of a pharmaceutical composition for oral use, the composition is provided in the form suitable for absorption through the alimentary tract and may be formulated as solid preparations such as tablets, capsules, powders, sugar-coated tablets, and granules, or liquid preparations such as syrups, suspensions and elixirs. The solid preparation can be formulated by selecting and adding from a pharmaceutical viewpoint an adjuvant, for example, a binder such as syrup, gum arabic, gelatin, sorbitol, tragacanth, or polyvinyl pyrrolidone; a vehicle such as lactose, sugar, cornstarch, calcium phosphate, sorbitol, or glycine; a lubricant such as magnesium stearate, talc, polyethylene glycol, or silica; a disintegrator such as potato starch; a wetting agent; a stabilizer; and a taste modifier. For the liquid preparation, a suspending agent such as sorbitol, syrup, methyl cellulose, glucose/sugar syrup, gelatin, hydroxyethyl cellulose, carboxymethyl cellulose, aluminum stearate gel, or a hydrogenated edible oil; an emulsifier; and an antiseptic such as methyl p-hydroxybenzoate, propyl p-hydroxybenzoate, or sorbic acid can be used, if desired, as an adjuvant.

In order to obtain a pharmaceutical preparation for injection use, a pH adjusting agent, a buffer, a stabilizer, a preservative, a solubilizer or the like is added, if desired, to the compounds of formula [I] of the present invention which form active ingredients of the drugs of the invention to formulate a preparation for subcutaneous, intramuscular or intravenous injection by a conventional method.

Hereinafter, the methods for testing the antitumor activities of the compound of the present invention represented by formula [I] and the results obtained according to said methods will be set forth.

TEST EXAMPLE 1

In vitro anti-proliferative activity against mouse tumor cell lines

TEST METHOD 1

1. L1210 mouse leukemia cells are cultivated in RPMI1640 medium supplemented with 10% fetal bovine serum, and the resultant cells are diluted with the same medium in the logarithmic growth phase to a concentration of $1.6 \times 10^5$ cells/ml.

2. To test tubes each containing 0.9 ml of the above obtained diluted cell suspension is added 0.1 ml each of test solutions serially diluted with a culture medium or phosphate-buffered saline (PBS), and the mixture is incubated in a 2% $CO_2$-incubator at 37° C. for 48 hours.

3. After incubation, the number of the cells in each tube is counted with a Coulter counter (Model ZB, Coulter Electronics), and the growth inhibition percent (%) of the cells at each concentration of a test compound is calculated from the following equation:

$$\text{Growth inhibition percent (\%)} = \left(1 - \frac{Tx - Co}{Cx - Co}\right) \times 100$$

Tx: Number of the cells in a test tube containing a test compound as counted upon completion of the incubation (cells/ml)

Cx: Number of the cells in a test tube containing no test compound as counted upon completion of the incubation (cells/ml)

Co: Number of the cells in a test tube containing no test compound as counted at the initiation of the incubation (cells/ml)

4. The concentration of the test compound, which causes cell growth inhibition by 50%, is determined by the graph showing the relationship between the growth inhibition percent and the concentration of the test compound, and is defined as 50% inhibitory concentration ($IC_{50}$).

Results:

| Test compound of formula [I] | | | |
|---|---|---|---|
| R | A | $R^1$ | $IC_{50}$ ($\mu$g/ml) |
|  | $CONH_2$ | H | 0.18 |
| | | $CH_2OH$ | 0.7 |
| | | $CH_2CH_2OH$ | 1.28 |
| | | $C_3H_7$ | 2.92 |
| | CN | H | 1.9 |
| | | $CH_2OH$ | 4.1 |
| | | $CH_2CH_2OH$ | 3.3 |
| H | $CONH_2$ | H | 4.0 |
| | CN | H | 2.9 |

Test Method 2:

1. Mouse lymphoma cell line P388 or mouse sarcoma 180 is suspended in RPMI1640 medium supplemented with 10% fetal bovine serum and 2 $\mu$M 2-hydroxyethyl disulfide to a concentration of $10^5$ cells/ml. Test compounds are serially diluted with the same medium.

2. 0.5 ml of the cell suspension thus obtained is admixed with 0.5 ml of the medium or the test compound solution, and the mixture is incubated in a 5% $CO_2$-incubator at 37° C. for 48 hours. The incubation is carried out in glass culture tubes.

3. At the end of incubation, the number of the cells in each tube is counted with a Coulter counter (Model ZB, Coulter Electronics), and the growth inhibition percent (%) is calculated from the same equation as in Test Method 1.

4. The $IC_{50}$ value is obtained as in Test Method I.

Results:

| Anti-proliferative activity of ethynylimidazole derivatives | | |
|---|---|---|
| | $IC_{50}$ (μg/ml) | |
| Ethynylimidazole derivatives | P388 | Sarcoma 180 |
| 5-ethynyl-1-β-D-ribofuranosyl-imidazole-4-carboxamide | 0.16 | 0.10 |
| 5-ethynylimidazole-4-carboxamide | 4.37 | 1.39 |
| 5-ethynyl-1-β-D-ribofuranosyl-imidazole-4-carbonitrile | 0.93 | 0.80 |
| 5-ethynylimidazole-4-carbonitrile | 14.1 | 9.92 |

TEST EXAMPLE 2

In vitro anti-proliferative activity against human tumor cell lines

Test Compound:
5-ethynyl-1-β-D-ribofuranosylimidazole-4-carboxamide

Test Method:

A variety of human tumor cell lines are suspended in media specified according to the species of the cell lines to predetermined cell concentrations as shown in the following Table.

1 ml of the resulting cell suspension is seeded into each well of a 24 multi-well plate and incubated in a 5% CO2-incubator at 37° C. for 24 hours. The culture medium is then replaced by a medium containing no test compound or by an appropriate amount of a serially diluted test compound solution. After additional incubation in a 5% CO2-incubator at 37° C. for 72 hours, the cells are washed with phosphate-buffered saline (PBS), and treated with PBS containing trypsin (0.125%) and EDTA (0.05%) at 37° C. for 1 hour to prepare a cell suspension. The number of the cells in each well is counted with a Coulter counter (Model ZB, Coulter Electronics), and the growth inhibition percent (%) of the cells at each concentration of a test compound is determined by the following equation:

$$\text{Growth inhibition percent (\%)} = \left(1 - \frac{Tx - Co}{Cx - Co}\right) \times 100$$

Tx: Number of the cells in a well containing a test compound as counted upon completion of the incubation (cells/ml)

Cx: Number of the cells in a well containing no test compound as counted upon completion of the incubation (cells/ml)

Co: Number of the cells in a well containing no test compound as counted at the initiation of the incubation (cells/ml)

The $IC_{50}$ value is obtained as in Test Method I.

| Human tumor cell lines, their origins, culture media, and seeded cell concentrations | | | |
|---|---|---|---|
| Cell line | Origin | Culture medium* | Seeded cell Concentration (cells/ml) |
| MG-63 | Osteogenic sarcoma | Eagle's MEM | $2.0 \times 10^4$ |
| PANC-1 | Pancreatic carcinoma | Eagle's MEM | $2.0 \times 10^4$ |
| KB | Nasopharyngeal carcinoma | Eagle's MEM | $2.0 \times 10^4$ |
| WiDr | Colon adenocarcinoma | Eagle's MEM | $2.0 \times 10^4$ |
| KU-2 | Renal cell carcinoma | Eagle's MEM | $2.5 \times 10^4$ |
| SK-MES-1 | Lung Squamous carcinoma | Eagle's MEM** | $3.0 \times 10^4$ |
| A549 | Lung carcinoma | Dulbecco's MEM | $2.5 \times 10^4$ |
| T24 | Bladder trasitional-cell carcinoma | McCoy's 5A | $2.5 \times 10^4$ |
| U-2OS | Osteogenic sarcoma | McCoy's 5A | $2.0 \times 10^4$ |
| HeLa | Cervical carcinoma | Eagle's MEM | $2.5 \times 10^4$ |
| HEp-2 | Laryngeal carcinoma | Eagle's MEM | $3.0 \times 10^4$ |
| Du145 | Prostate carcinoma | Eagle's MEM | $2.0 \times 10^4$ |
| QG-56 | Lung squamous carcinoma | RPMI 1640 | $3.0 \times 10^4$ |
| PC-3 | Prostate adenocarcinoma | RPMI 1640 | $2.5 \times 10^4$ |

*All the culture media are supplemented with 10% fetal bovine serum, penicillin and streptomycin
**This culture medium is supplemented with sodium pyruvate and non-essential amino acids.

Results:

| Anti-proliferative activity of 5-ethynyl-1-β-D-ribofuranosylimidazole-4-carboxamide against human tumor cell lines | | |
|---|---|---|
| Cell line | Origin | $IC_{50}$ (μg/ml) |
| MG-63 | Osteogenic sarcoma | 0.38 |
| PANC-1 | Pancreatic carcinoma | 0.90 |
| KB | Nasopharyngeal carcinoma | 0.33 |
| WiDr | Colon adenocarcinoma | 0.46 |
| KU-2 | Renal cell carcinoma | <0.10 |
| SK-MES-1 | Lung squamous carcinoma | 0.26 |
| A549 | Lung carcinoma | 0.37 |
| T24 | Bladder trasitional-cell carcinoma | 0.37 |
| U-2OS | Osteogenic sarcoma | 0.62 |
| HeLa | Cervical carcinoma | 0.30 |
| HEp-2 | Laryngeal carcinoma | 0.47 |
| Du145 | Prostate carcinoma | <0.10 |
| QG-56 | Lung squamous carcinoma | 0.37 |
| PC-3 | Prostate adenocarcinoma | 0.80 |

TEST EXAMPLE 3

In vivo antitumor activity against sarcoma 180 intracutaneously implanted into BALB/c mice Test Method:

Three million ($3 \times 10^6$) Sarcoma 180 cells are intracutaneously implanted at the ventral site of BALB/c mice (male, 5 weeks old). Eight days after the implantation when the tumor volume reached 200 to 300 mm$^3$, the mice are divided into groups (6 mice/group), and the treatment with a test drug was started. The test drug is dissolved in distilled water and intravenously administered to the mice at a rate of 0.1 ml per 10 g of the body weight thereof. In accordance with two different schedules, 5-ethynyl-1-β-D-ribofuranosylimidazole-4-carboxamide is administered once or three times, i.e., once at a dose of 250 mg/kg on day 8 (single-dose group) or three times at a dose of 125 mg/kg on days 8, 12 and 16 (multiple-dose group).

Each mouse is weighed, and the width (a and length (b mm) of the tumor thereof are measured twice a week to determine the tumor volume (A mm$^3$) from the following equation:

$$A = a^2 \times b/2$$

Subsequently, the tumor growth rate (R) is determined as follows on the basis of the tumor volume ($A_8$) on day 8 after the implantation of the tumor cells:

$$R = A/A_8$$

R: Tumor growth rate after a predetermined period from the tumor implantation
A: Tumor volume after a predetermined period from the tumor implantation
$A_8$L Tumor volume as determined 8 days after the tumor implantation T/C(%) is further obtained from the following equation by comparison between the tumor growth rate in the test group (Rt) and that in the control group (Rc):

$$T/C(\%) = (Rt/Rc) \times 100$$

Results:

As is apparent from the Table below, 5-ethynyl-1-β-D-ribofuranosylimidazole-4-carboxamide, both when administered once at a dose of 250 mg/kg and at a dose of 125 mg/kg every 4 days 3 times in total, exhibited a remarkable antitumor activity against sarcoma 180 iontracutaneously implanted at the ventral site of BALB/c mice.

mice (BALB/c-nu/nu, female, 5 weeks old). Ten days after the implantation when the tumor volume reaches 150 to 300 mm$^3$, the mice are divided into groups (6 mice/group), and the treatment with a test drug was started.

5-Ethynyl-1-β-D-ribofuranosylimidazole-4-carboxamide is dissolved in distilled water and intravenously administered to the mice at a dose of 125 mg/kg on days 10, 14 and 18 after the implantation of the tumor, the volume of the drug solution being 0.1 ml per 10 g of the body weight of the mouse.

Each mouse is weighed, and width (a mm) and length (b mm) of the tumor thereof are measured twice a week to determine the tumor volume (A mm$^3$) from the following equation:

$$A = a^2 \times b/2$$

Subsequently, the tumor growth rate (R) is determined as follows on the basis of the tumor volume ($A_{10}$) on day 10 after the implantation of the tumor cells:

$$R = A/A_{10}$$

R: Tumor growth rate after a predetermined period from the tumor implantation
A: Tumor volume after a predetermined period from the tumor implantation
$A_{10}$: Tumor volume as determined 10 days after the tumor implantation T/C (%) is further obtained from the following equation by comparison between the tumor growth rate in the test group (Rt) and that in the control group (Rc):

$$T/C(\%) = (Rt/Rc) \times 100$$

| | In vivo antitumor activity of 5-ethynyl-1-β-D-ribofuranosylimidazole-4-carboxamide against sarcoma 180 implanted in BALB/c mice | | | | | | | |
|---|---|---|---|---|---|---|---|---|
| Group | Measured quantity | \multicolumn{8}{c}{Day after tumor implantation} |
| | | 8 | 12 | 15 | 19 | 22 | 26 | 29 | 33 |
| Control | Tumor growth rate (Rc) | 1.0 | 1.8 | 2.9 | 4.3 | 7.2 | 12 | 17 | 21 |
| | Body weight (g) | 26 | 26 | 27 | 26 | 28 | 28 | 28 | 29 |
| single-dose group | Tumor growth rate (Rt) | 1.0 | 1.2* | 1.3* | 2.0* | 2.4* | 4.7* | 6.6* | 9.5* |
| | T/C (%) | 100 | 65* | 45* | 46* | 34* | 39* | 39* | 45* |
| | Body weight (g) | 25 | 24 | 25 | 25 | 26 | 26 | 26 | 27 |
| multiple-dose group | Tumor growth rate (Rt) | 1.0 | 1.5 | 1.5* | 1.9* | 2.6* | 4.7* | 7.0* | 11 |
| | T/C (%) | 100 | 81 | 51* | 45* | 37* | 39* | 42* | 53 |
| | Body weight (g) | 26 | 26 | 25 | 25 | 26 | 26 | 26 | 27 |

Single-dose group: 250 mg/kg of the drug was intravenously administered on day 8 after the tumor implantation.
Multiple-dose group: 125 mg/kg of the drug was intravenously administered on days 8, 12 and 16 after the tumor implantation.
*The figures were significantly different from those for the control group with P < 0.05 (t-test).

TEST EXAMPLE 4

In vivo antitumor activity against human gastric cancer cells, 4-1ST, subcutaneously implanted into nude mice Test Method:

Human gastric cancer cells, 4-1ST(ca. 8 mm$^3$), are subcutaneously implanted at the ventral site of nude Results:

As is noted from the Table below, 5-ethynyl-1-β-D-ribofuranosylimidazole-4-carboxamide, when administered at a dose of 125 mg/kg every 4 days 3 times in total, showed a remarkable antitumor activity against human gastric cancer cells, 4-1ST, subcutaneously implanted at the ventral site of nude mice.

| Group | Measured quantity | Day after tumor implantation |  |  |  |  |  |  |  |
|---|---|---|---|---|---|---|---|---|---|
|  |  | 10 | 14 | 17 | 22 | 25 | 28 | 31 | 35 |
| Control | Tumor growth rate (Rc) | 1.0 | 4.5 | 7.6 | 13 | 19 | 24 | 28 | 39 |
|  | Body weight (g) | 20 | 21 | 22 | 23 | 23 | 23 | 24 | 23 |
| Test group | Tumor growth rate (Rt) | 1.0 | 3.0 | 5.1 | 8.0* | 12* | 16 | 20 | 30 |
|  | T/C (%) | 100 | 67 | 67 | 60* | 63* | 67 | 71 | 77 |
|  | Body weight (g) | 20 | 21 | 21 | 22 | 23 | 23 | 24 | 23 |

In vivo antitumor activity of 5-ethynyl-1-$\beta$-D-ribofuranosylimidazole-4-carboxamide against human gastric cancer cells, 4-1ST, implanted in nude mice Test group: 125 mg/kg of the drug was intravenously administered on days 10, 14 and 18 after the tumor implantation.
*The figures were significantly different from those for the control group with P < 0.05 (t-test).

EXAMPLE

In the following, the present invention is described in detail with reference to Reference Examples and Examples.

REFERENCE EXAMPLE A1

Synthesis of trimethyl[(tributylstannyl)ethynyl]-silane [Formula [IV]: Y=trimethylsilyl, Z=butyl]

Under argon stream, 3.53 ml (25 mmol) of trimethylsilylacetylene was dissolved in 25 ml of tetrahydrofuran and cooled to −78° C. Into the solution was added dropwise 14.9 ml (24 mmol) of butyllithiumhexane solution, and the reaction was carried out with stirring for 30 minutes. Then, 6.5 ml (24 mmol) of tributyltin chloride was added dropwise, and the reaction was carried out with stirring for 22 hours, while elevating gradually the temperature of the reaction mixture to room temperature. After the reaction, the solvent was evaporated and the residue was distilled under reduced pressure (0.6 mm Hg, 100°–102° C.) to obtain 4.84 g of a transparent liquid (yield: 52.2%).

REFERENCE EXAMPLE A2

Synthesis of 5-iodo-1-(2,3,5-tri-O-acetyl-$\beta$-D-ribofuranosyl)imidazole-4-carboxamide [Formula [IIc]or [IId]: A =carbamoyl (CONH$_2$), X=iodine atom, R or R'=2,3,5-tri-O-acetyl-D-ribose]

To a suspension of 5.16 g (20 mmol) of 5-amino-1-($\beta$-D-ribofuranosyl)imidazole-4-carboxamide in 50 ml of acetonitrile were added 7.6 ml (80 mmol) of acetic anhydride, 11.3 ml (80 mmol) of triethylamine and 50 mg of 4-dimethylaminopyridine, and the reaction was carried out with stirring at room temperature. When 5-amino-1-($\beta$-D-ribofuranosyl)imidazole-4-carboxamide was completely dissolved (after about 30 minutes), 5 ml of methanol was added, the solvent was evaporated, and the residue obtained was partitioned 4 times with water-chloroform (150 ml: 70 ml). The organic layer was dried over anhydrous sodium sulfate, which step was followed by evaporation of the solvent to obtain a colorless glutinous substance.

Next, the glutinous substance obtained was subjected to azeotropic distillation with ethanol 5 times and then dissolved in 100 ml of diiodomethane in an oil bath of 100° C., and further 10 ml of isoamyl nitrite was added to carry out the reaction for 30 minutes After the reaction, the reaction mixture was adsorbed onto a silica gel column (3.6×40 cm), which was then eluted with a 1% –4% ethanol-chloroform solvent mixture, and the fractions containing the desired compound were collected. After evaporation of the solvent, acetone was added to the residue to obtain 5.42 g of a bright yellow foamy substance (yield: 54.7%).

EXAMPLE A1

Synthesis of 5-ethynyl-1-$\beta$-D-ribofuranosylimidazole-4-carboxamide [Formula [I]: A=CONH$_2$, R$^1$=hydrogen atom, R=D-ribose]

(1) Synthesis of 5-(2-trimethylsilyl-1-ethyn-1-yl)-1-(2,3,5-tri-0-acetyl-$\beta$-D-ribofuranosyl)imidazole-4-carboxamide 5-Iodo-1-(2,3,5-tri-0-acetyl-$\beta$-D-ribofuranosyl)-imidazole-4-carboxamide (990 mg, 2 mmol) obtained in Reference Example A2 and 36 mg (0.1 mmol) of bis(benzonitrile)palladium dichloride were charged into a sealed tube and dissolved in 7 ml of acetonitrile under argon gas stream. To the solution was further added 850 mg (2.2 mmol) of trimethyl[(tributylstannyl)ethynyl]silane obtained in Reference Example A1, and the reaction was carried out in an oil bath at 100° C for 17 hours. After the reaction, the reaction mixture was filtered through Celite, washed with ethanol and then the solvent was evaporated. The residue obtained was adsorbed onto a silica gel column (2.7 x 18 cm) and eluted with hexane-ethyl acetate to obtain 668 mg of a glutinous substance (yield: 71.8%).

UV-ray absorption spectrum (UV) (in methanol) $\gamma$max 270 nm, 269 nm (acidic), 261 nm (basic)

Mass spectrum (MS): 465 (molecular ion peak (M$^+$))

$^1$H-NMR (CDCl$_3$) 7.73 (S, 1H, H-2), 6.03 (d, 1H, H-1', J1',2'=4.63), 2.17, 2.11, 2.10 (s, each 3H, acetyl), 0.30 (s, 9H, trimethylsilyl)

(2) Synthesis of 5-ethynyl-1-$\beta$-D-ribofuranosyl-imidazole-4-carboxamide 400 mg of the glutinous substance obtained in (1) was added to a solvent mixture of aqueous ammonia and methanol and, after the mixture was left to stand overnight, the solvent was evaporated. The residue obtained was adsorbed onto a silica gel column (2.3×13 cm), eluted with a 5–10% ethanol-chloroform solvent mixture and crystallized from ethanol to obtain 200 mg of white crystals (yield: 87.1%).

m.p.: 182°–185° C.

Elemental analysis (for C₁₁H₁₃N₃O₅) Calcd. C 49.44%, H 4.90%, N 15.72%., Found C 49.45%, H 4.95%, N 15.62%.
MS: 267 (M⁺)
¹H-NMR (DMSO-d6): 4.86 (s, 1H, —C≡CH)

EXAMPLE A2

Synthesis of 5-(phenylethyn-1-yl)-1-β-D-ribofuranosylimidazole-4-carboxamide [Formula [I]: A=CONH₂, R¹=phenyl, R=D-ribose]

(1) Synthesis of 5-(phenylethyn-1-yl)-1-(2,3,5-tri-O-acetyl-β-D-ribofuranosyl)imidazole-4-carboxamide 5-Iodo-1-(2,3,5-tri-0-acetyl-β-D-ribofuranosyl)-imidazole-4-carboxamide (495 mg, 1 mmol) obtained in Reference Example A2 and 36 mg (0.1 mmol) of bis(-benzonitrile)palladium dichloride were charged into a sealed tube and dissolved in 5 ml of acetonitrile under argon gas stream. To the solution was further added 0.16 ml (1.2 mmol) of triethylamine and 0.13 ml (1.2 mmol) of phenylacetylene, and the reaction was carried out in an oil bath at 100° C. for 4 hours. After the reaction, the reaction mixture was filtered through Celite, further washed with ethanol and then the solvent was evaporated. The residue obtained was adsorbed onto a silica gel column (2.7×35 cm) and eluted with a 0–8% ethanolchloroform solvent mixture to obtain 740 mg of the desired compound (yield: 78.9%).

UV (H₂O): 317 nm and 300 nm (neutral, acidic, basic)
MS: 469 (M⁺)
¹H-NMR (CDCl₃): 7 60 (m, 2H,

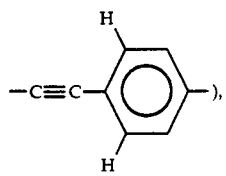

), 7.37 (m, 2H,

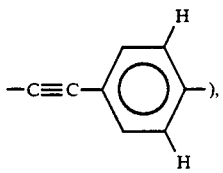

), 2.15, 2.13, 2.02 (s, each 3H, acetyl)

(2) Synthesis of 5-(phenylethyn-1-yl)-1-β-D-ribofuranosylimidazole-4-carboxamide A solution of 360 mg of the compound obtained in (1) dissolved in a solvent mixture of aqueous ammonia and methanol was left to stand overnight, then the solvent was evaporated, and the residue was adsorbed onto a silica gel column (1.8 x 14 cm) and eluted with a 5 - 20% ethanol-chloroform solvent mixture, followed by crystallization from ethanol-ether to obtain 198 mg of white crystals (yield 75.2%).

m.p.: 168°–169° C.
Elemental analysis (for C₁₇H₁₇N₃O₅·¼H₂O): Calcd. C 58.70%, H 5.07%, N 12.08%]Found C 58.91%, H 5.05%, N 11.95%.
MS: 343 (M⁺)
1H-NMR (DMSO-d6): 7.49 (m, 6H, —C≡CC₆H₅, —CONH)

EXAMPLES A3–A6

By use of 3-hydroxy-1-propyne, 4-hydroxy-1-butyne, 1-pentyne and 1-hexyne in place of phenylacetylene of Example A2 (1), the reactions were carried out in the same manner as in Example 2A (1) to obtain the desired compounds. The results are shown in Table A1.

Next, the compounds thus obtained were treated in the same manner as in Example A2 (2), except that the compound was crystallized by use of ethanol-hexane as the crystallization solvent in Example A5 and no crystallization was effected in Example A6, to obtain the desired compounds.

The results are shown in Table A2 and Table A3.

TABLE A1

| Example | R¹ | Yield (%) | UV (λₘₐₓ) | MS(M⁺) | ¹H-NMR (CDCl₃) |
|---|---|---|---|---|---|
| A3 | —CH₂OH | 93.6 | (in water) 265 nm 259 (acidic) 266 (basic) | 423 | 4.57 (bs, 2H, —CH₂OH) 2.18 (s, 3H, acetyl) 2.15 (s, 3H, acetyl) 2.13 (s, 3H, acetyl) |
| A4 | —(CH₂)₂OH | 92.7 | (in water) 267 260 (acidic) 267 (basic) | 437 | 3.88 (m, 2H, —CH₂OH) 2.75 (m, 2H, —C≡CH₂—) 2.17 (s, 3H, acetyl) 2.14 (s, 3H, acetyl) 2.12 (s, 3H, acetyl) |
| A5 | —C₃H₇ | 74.5 | (in methanol) 265 257 (acidic) 267 (basic) | 435 | 2.54 (m, 2H, —C≡CH₂—) 2.16 (s, 3H, acetyl) 2.11 (s, 3H, acetyl) 2.10 (s, 3H, acetyl) 1.79–1.02 (m, 5H, —CH₂CH₃) |
| A6 | —C₄H₉ | 73.1 | (in methanol) 256 257 (acidic) 267 (basic) | 449 | 2.56 (m, 2H, —C≡CH₂—) 2.16 (s, 3H, acetyl) 2.12 (s, 3H, acetyl) 2.10 (s, 3H, acetyl) 1.69–0.88 (m, 7H, —CH₂CH₂CH₃) |

In the Table, A is all carbamoyl and R is all 2,3,5-tri-O-acetyl-D-ribose in the compound of formula [I].

TABLE A2

| Example | R¹ | Yield (%) | m.p. (°C.) | ¹H-NMR |
|---|---|---|---|---|
| A3 | —CH₂OH | 85.5 | 148–149 | 5.45 (t, 1H, —CH₂OH, J=6.10) 4.37 (d, 2H, —CH₂OH, J=6.0) |

TABLE A2-continued

| Example | R$^1$ | Yield (%) | m.p. (°C.) | $^1$H-NMR |
|---|---|---|---|---|
| A4 | —(CH$_2$)$_2$OH | 78.7 | 156–158 | 5.00 (m, 2H, 5'-O$\underline{H}$, —CH$_2$O$\underline{H}$) |
| | | | | 3.59 (m, 4H, H-5', —C$\underline{H_2}$OH) |
| | | | | 2.64 (m, 2H, —C≡CC$\underline{H_2}$—) |
| A5 | —C$_3$H$_7$ | 82.2 | 172–174 | 2.42 (m, 2H, —C≡CC$\underline{H_2}$—) |
| | | | | 1.69–0.95 (m, 5H, —C$\underline{H_2}$C$\underline{H_3}$) |
| A6 | —C$_4$H$_9$ | 78.3 | — | 2.50 (m, 2H, —C≡CC$\underline{H_2}$—) |
| | | | | 1.53–0.91 (m, 7H, —C$\underline{H_2}$—C$\underline{H_2}$CH$_3$) |

In the Table, A is all carbamoyl and R is all D-ribose in the compound of formula [I].

TABLE A3

| Example | R$^1$ | MS | Elemental Analysis Calcd. (%) C, H, N Found (%) C, H, N |
|---|---|---|---|
| A3 | —CH$_2$OH | 280 (M$^+$—OH) | 48.48, 5.09, 14.14 |
| | | | 48.45, 5.13, 13.99 |
| A4 | —(CH$_2$)$_2$OH | 311 (M$^+$) | 50.16, 5.51, 13.50 |
| | | | 50.18, 5.52, 13.50 |
| A5 | —C$_3$H$_7$ | 309 (M$^+$) | 54.36, 6.19, 13.58 |
| | | | 54.49, 6.17, 13.48 |
| A6 | —C$_4$H$_9$ | 323 (M$^+$) | — |

In the Table, A is all carbamoyl and R is all D-ribose in the compound of formula [I].

EXAMPLE A7

Tablet

| | |
|---|---|
| 5-Ethynyl-1-β-D-ribofuranosylimidazole-4-carboxamide | 10 g |
| Corn starch | 65 g |
| Carboxymethylcellulose | 20 g |
| Polyvinyl pyrrolidone | 3 g |
| Calcium stearate | 2 g |
| Total: | 100 g |

Tablets each weighing 100 mg are prepared in a conventional manner. Each tablet contains 10 mg of 5-ethynyl-1-β-D-ribofuranosylimidazole-4-carboxamide.

EXAMPLE A8

Powder & Capsule

| | |
|---|---|
| 5-(3-Hydroxy-1-propyn-1-yl)-1-β-D-ribofuranosylimidazole-4-carboxamide | 20 g |
| Crystalline cellulose | 80 g |
| Total: | 100 g |

Both powders are mixed to prepare a powder. Also, 100 mg of the powder is filled into a No. 5 hard capsule to prepare a capsule.

EXAMPLE B1

Synthesis of 5-iodo-1-(2,3,5-tri-0-acetyl-β-D-ribofuranosyl)imidazole-4-carbonitrile [Formula [IIg]: X=iodine, R2=acetyl, R3=OR2]

10.88 g (29.7 mmol) of 5-amino-1-(2,3,5-tri-O-acetyl-β-D-ribofuranosyl)imidazole-4-carbonitrile was dissolved in 150 ml of diiodomethane in an oil bath at 100° C., and further 15 ml of isoamyl nitrite was added to cause reaction for 30 minutes. After the reaction, the reaction mixture was adsorbed onto a silica gel column (3.6×36 cm) and eluted with 1–4% ethanol-chloroform to obtain the fractions containing the desired compound, which were recrystallized from ethanol to obtain 9.86 g of the desired compound (yield: 69.6%).

m.p.: 139°–141° C.

UV-ray absorption spectrum (UV): 235 nm (neutral)

Elemental analysis (for C$_{15}$H$_{16}$N$_3$O$_7$I): Calcd. C 37.74%, H 3.35%, N 8.81%., Found C 37.76%, H 3.18%, N 8.74%.

EXAMPLES B2–B5

(1) Synthesis of 5-alkynyl-1-(2,3,5-tri-O-acetyl-β-D-ribofuranosyl)imidazole-4-carbonitrile [Formula [I]: A=cyano(CN), R=2,3,5-tri-0-acetyl ribose]

477 mg of 5-iodo-1-(2,3,5-tri-0-acetyl-β-D-ribofuranosyl)imidazole-4-carbonitrile and 18 mg (5 mol %) of bis(benzonitrile) palladium dichloride were charged into a sealed tube and dissolved in acetonitrile under argon gas stream. To the solution were added 0.16 ml (1.2 mmol) of triethylamine and 1.2 mol of an acetylene derivative (phenylethyne, 3-hydroxy-1-propyne, 1-hexyne, trimethylsilylacetylene (trimethylsilylethyne)), and the reaction was carried out in an oil bath at 100° C. After the reaction, the reaction mixture was filtered through Celite, washed with ethanol and then purified through a silica gel column. The identification data of the compounds obtained are shown in Table B1.

TABLE B1

| Example | Compound (R$^1$) | Reaction time (h) | Yield (%) | Mass analysis (M$^+$) | $^1$H-NMR(CDCl$_3$) |
|---|---|---|---|---|---|
| B2(1) | —C$_6$H$_5$ | 3.5 | 97.3 | 451 | 7.49 (m, 5H, —C$_6\underline{H}_5$) |
| | | | | | 2.14 (s, 3H, acetyl) |
| | | | | | 2.13 (s, 3H, acetyl) |
| | | | | | 2.07 (s, 3H, acetyl) |
| B3(1) | —CH$_2$OH | 2.0 | 77.0 | 405 | 4.58 (d, 2H, —C≡CC$\underline{H_2}$—, J=6.59) |
| | | | | | 2.68 (t, 1H, —CH$_2$O$\underline{H}$, J=6.59) |
| | | | | | 2.14 (s, 3H×3, acetyl) |
| B4(1) | —(CH$_2$)$_3$CH$_3$ | 5.5 | 83.4 | 431 | 2.54 (t, 2H, —C≡CC$\underline{H_2}$—, J=6.59) |
| | | | | | 2.13 (s, 3H×3, acetyl) |
| | | | | | 1.57 (m, 4H, —C$\underline{H_2}$C$\underline{H_2}$—) |
| | | | | | 0.97 (t, 3H, —C$\underline{H_3}$, J=6.83) |
| B5(1) | —Si(CH$_3$)$_3$ | 16 | 76.4 | 447 | 2.12 (s, 3H×3, acetyl) |

TABLE B1-continued

| Example | Compound (R¹) | Reaction time (h) | Yield (%) | Mass analysis (M⁺) | ¹H-NMR(CDCl₃) |
|---------|---------------|-------------------|-----------|--------------------|----------------|
|         |               |                   |           |                    | 0.30 (s, 9H, —Si(CH₃)₃) |

In the Table, A is all cyano and R is all 2,3,5-tri-O-acetyl-D-ribose in the compound of formula [I].

(2) Synthesis of 5-alkynyl-1-$\beta$-D-ribofuranosylimidazole-4-carbonitrile [Formula [I]: A=CN, R=D-ribose]

The compound obtained in the above (1) was dissolved in a solvent mixture of aqueous ammonia and methanol and the reaction was carried out at room temperature for 4 to 12 hours. After the reaction, the solvent was evaporated and the residue obtained was purified through a silica gel column to obtain the desired compound. The identification data of the compounds obtained are shown in Table B2.

TABLE B2

| Example | Compound (R¹) | Yield (%) | Mass analysis (M⁺) | m.p. (°C.) | ¹H-NMR(DMSO-d6) |
|---------|---------------|-----------|--------------------|------------|------------------|
| B2(2) | —C₆H₅ | Quantitative (ca. 100) | 325 | 187–188 | 7.60 (m, 5H, —C₆$\underline{H}$₅) |
| B3(2) | —CH₂OH | 84.8 | 279 | 138–139 | 5.61 (t, 1H, —CH₂O$\underline{H}$, J=6.11) 4.43 (d, 2H, —C$\underline{H}$₂OH, J=6.11) |
| B4(2) | —(CH₂)₃CH₃ | 89.9 | 305 | 140–141 | 2.60 (t, 2H, —C≡CC$\underline{H}$₂—, J=5.84) 1.53 (m, 4H, —C$\underline{H}$₂C$\underline{H}$₂—) 0.92 (t, 3H, —C$\underline{H}$₃, J=6.59) |
| B5(2) | —H | Quantitative (ca. 100) | 249 | — | 5.35 (s, 1H, —C≡C$\underline{H}$) |

In the Table, A is all cyano and R is all D-ribose in the compound of formula [I].

EXAMPLE B6 Tablet

| | |
|---|---|
| 5-Ethynyl-1-$\beta$-D-ribofuranosylimidazole-4-carbonitrile | 10 g |
| Corn starch | 65 g |
| Carboxymethylcellulose | 20 g |
| Polyvinyl pyrrolidone | 3 g |
| Calcium stearate | 2 g |
| Total: | 100 g |

Tablets each weighing 100 mg are prepared in a conventional manner. Each tablet contains 10 mg of 5 ethynyl-1-$\beta$-D-ribofuranosylimidazole-4-carbonitrile.

EXAMPLE B7 Powder & Capsule

| | |
|---|---|
| 5-(3-Hydroxy-1-propyn-1-yl)-1-$\beta$-D-ribofuranosylimidazole-4-carbonitrile | 20 g |
| Crystalline cellulose | 80 g |
| Total: | 100 g |

Both powders are mixed to prepare a powder. Also, 100 mg of the powder is filled into a No. 5 hard capsule to prepare a capsule.

EXAMPLE C1

Synthesis of 5-(phenylethyn-1-yl)-1-$\beta$-D-ribofuranosylimidazole-4-carboxamide [Formula [I]: A =CONH₂, R¹=phenyl, R=D-ribose]

To a solution of 10 mg (0.03 mmol) of 5-(phenylethyn-1-yl)-1-$\beta$-D-ribofuranosylimidazole-4-carbonitrile dissolved in 4 ml of aqueous ammoniamethanol (1:1 V/V) was added 0.2 ml of hydrogen peroxide, and the reaction was carried out with stirring at room temperature for 30 minutes. After the reaction, the solvent was evaporated and the residue was adsorbed onto a silica gel column (1.8×35 cm) and eluted with a 5-ethanol-chloroform solvent mixture to obtain 8.4 mg of 5-(phenylethyn-1-yl)-1-$\beta$-D-ribofuranosylimidazole-4-carboxamide (yield: 79.6%).

m.p.: 168°–169° C.

Elemental analysis (for $C_{17}H_{17}N_3O_5 \cdot \frac{1}{4}H_2$): Calcd. C 58.70%, H 5.07%, N 12.08%, Found C 58.71%, H 5.05%, N 11.93%.

EXAMPLE C2

Synthesis of 5-ethynyl-1-(2,3,5-tri-0-acetyl-$\beta$-D-ribofuranosyl-)imidazole-4-carboxamide [Formula [I]: A=CONH₂, R¹=hydrogen atom, R=2,3,5-tri-O-acetyl-D-ribose]

To a solution of 127 mg (0.51 mmol) of 5-ethynyl-1-$\beta$-D-ribofuranosylimidazole-4-carbonitrile dissolved in 6 ml of a solvent mixture of aqueous ammonia and methanol (1:1) was added 0.5 ml of hydrogen peroxide, and the reaction was carried out with stirring at room temperature for 45 minutes. After the reaction, the solvent was evaporated, and the residue was adsorbed onto a silica gel column and eluted with a 5 - 10% ethanol-chloroform solvent mixture, and crystallized from ethanol to obtain white crystals of 5-ethynyl-1-$\beta$-D-ribofuranosylimidazole-4-carboxamide.

m.p.: 182°–185° C.

Elemental analysis (for $C_{11}H_{13}N_3O_5$): Calcd. C 49.44%, H 4.90%, N 15.72%, Found C 49.45%, H 4.95%, N 15.62%.

The whole amount of said crystals was added to a solvent mixture of 4 ml of anhydrous acetonitrile, 5 mg of 4-dimethylaminopyridine, 0.28 ml of triethylamine and 0.19 ml of acetic anhydride, and the reaction was carried out with stirring at room temperature for 30 minutes, which step was followed further by addition of 1 ml of methanol to carry out the reaction for 5 minutes. After the reaction, the solvent was evaporated, and the residue was adsorbed onto a silica gel column (1.8 x 10 cm) and eluted with a 50 25% hexane-ethyl acetate eluent to obtain 154 mg of 5-ethynyl-1-(2,3,5-tri-O-acetyl-β-D-ribofuranosyl)imidazole-4-carboxamide (yield: 77.0%).

EXAMPLE D1

Synthesis of 5-ethynylimidazole-4-carbonitrile
[Formula [I]: A⊙CN, R¹=hydrogen atom, R=hydrogen atom]

A solution of 447 mg (1 mmol) of 5-trimethylsilylethynyl-1-(2,3,5-tri-O-acetyl-β-D-ribofuranosyl) imidazole-4-carbonitrile in a 1N hydrochloric acid-methanol (10 ml: 5 ml) solvent mixture was heated under reflux at 100° C. for 4 hours. After the reaction, the reaction solution was neutralized with 1N sodium hydroxide solution, silica gel powder was added, and the solvent was evaporated. The residue was adsorbed onto a silica gel column (2.7×13 cm), eluted with a 0–8% ethanol-chloroform solvent mixture, and crystallized from water-containing methanol to obtain 112 mg of pale yellow crystals of 5-ethynylimidazole-4-carbonitrile (yield: 95.7%).

m.p.: 169° C.

Elemental analysis (for $C_6H_3N_3$): Calcd. C 61.53%, H 2.58%, N 35.88%., Found C 61.50%, H 2.52%, N 35.78%.

UV($H_2O$): $\lambda_{max}$ 254 nm (neutral), 254 nm (acidic), 265 nm (basic)

MS: 117 (M⁺)

1H-NMR(DMSO-d6): 13.7(bs, 1H, H-1), 7.99(s, 1H, H-2), 5.02(s, 1H, C≡C$\underline{H}$)

EXAMPLE D2

Synthesis of 5-ethynylimidazole-4-carboxamide
[Formula [I]: A=CONH₂, R¹=hydrogen atom, R=hydrogen atom]

A solution of 200 mg (0.75 mmol) of 5-ethynyl-1-β-D-ribofuranosylimidazole-4-carboxamide in 5 ml of 1N hydrochloric acid solution was heated under reflux at 100° C. for 4 hours. After the reaction, the reaction solution was neutralized with 1N sodium hydroxide solution, silica gel powder was added, and the solvent was evaporated. The residue was adsorbed onto a silica gel column (2.7×11 cm), eluted with a 0–16% ethanol-chloroform solvent mixture, and crystallized from an ethanol-hexane solvent mixture to obtain 38 mg of pale yellow crystals of 5-ethynylimidazole-4-carboxamide (yield: 37.6%).

m.p.: 208°–209° C. (decomposed)

Elemental analysis (for $C_6H_5N_3O$): Calcd. C 53.33%, H 3.73%, N 31.10%., Found C 53.18%, H 3.66%, N 31.15%.

UV($H_2O$): $\lambda_{max}$ 262 nm (neutral), 249 nm (acidic), 279 nm (basic)

MS: 135 (M⁺)

1H-NMR(DMSO-d6): 13.0(bs, 1H, H-1), 7.71(s, 1H, H-2), 7.25, 7.22(bs, 2H, N$\underline{H_2}$) 4.52(s, 1H, C≡C$\underline{H}$)

EXAMPLE D3

Tablet

| 5-Ethynylimidazole-4-carbonitrile | 10 g |
|---|---|
| Corn starch | 65 g |
| Carboxymethylcellulose | 20 g |
| Polyvinyl pyrrolidone | 3 g |
| Calcium stearate | 2 g |
| Total: | 100 g |

Tablets each weighing 100 mg are prepared. Each tablet contains 10 mg of 5-ethynylimidazole-4-carbonitrile.

EXAMPLE D4

Powder & Capsule

| 5-Ethynylimidazole-4-carboxamide | 20 g |
|---|---|
| Crystalline cellulose | 80 g |
| Total: | 100 g |

Both powders are mixed to prepare a powder. Also, 100 mg of the powder is filled into a No. 5 hard capsule to prepare a capsule.

REFERENCE EXAMPLE E1

(1) Synthesis of 5-amino-1-(3,5-O-TIPDS-β-D-ribofuranosyl)imidazole-4-carbonitrile To a solution of 6.0 g (25 mmol) of 5-amino-1-β-D-ribofuranosylimidazole-4-carbonitrile in 60 ml of pyridine was added 8.7 ml (1.1 equivalents) of 1,3-dichloro-1,1,3,3-tetraisopropyldisiloxane (TIPDS Cl₂) dropwise over 1.5 hours under ice-cooled conditions (0° C.), and the mixture was stirred for 4.5 hours. To the reaction solution was added an appropriate amount of methanol, and the resulting solution was stirred for 5 minutes. The solvent was evaporated while the residue was partitioned between 100 ml of ethyl acetate and 50 ml of water to wash the organic layer. The same procedure was repeated with addition of another 50 ml of water, and the organic layer was dried with sodium sulfate and the solvent was then evaporated under reduced pressure. The residue was adsorbed onto a silica gel column (3.6×27 cm), eluted with a 0–2% ethanol-chloroform solvent mixture, and crystallized from n-hexane to obtain 10.43 g of the desired compound in the form of a crystalline powder (yield: 86.6%).

m.p.: 160°–162° C.

Elemental analysis (for $C_{21}H_{38}N_4O_5Si_2$): Calcd. C 52.25%, H 7.93%, N 11.61%., Found C 52.20%, H 7.94%, N 11.54%

MS(m/z): 482 (M⁺)

1H-NMR(CDCl₃+D₂O):7.16(s, 1H, H-2), 5.55(d, 1H, H-1'), 4.64(dd, 1H, H-2'), 4.06(m, 4H, H-3',4',5',5''), 1.09(m, 28H, TIPDS)

(2) Synthesis of 5-amino-1-(3,5-O-TIPDS-2-O-thiocarbonylimidazolyl-β-D-ribofuranosyl)imidazole-4-carbonitrile To a solution of 8.311 g (17.2 mmol) of the compound obtained in (1) above in 100 ml of dimethylformamide (DMF) was added 6.81 g (2 equivalents) of thiocarbonyldiimidazole, and the mixture was stirred at room temperature for 10 hours. The solvent was evaporated while the residue was suspended in ethanol and washed thoroughly with ethanol to obtain 7.75 g of the desired compound in the form of a powder (yield: 75.9%).

Elemental analysis (for $C_{25}H_{40}N_6O_5SSi_2$): Calcd. C 50.65%, H 6.80%, N 14.17%, Found C 50.37%, H 6.71%, N 14.25%.

MS(m/z): 592 (M⁺)

1H-NMR(CDCl₃) 8.35, 7.65, 7.10 (m, 3H, thiocarbonylimidazolyl), 7.30(s, 1H, H-2), 5.82(m, 2H, H-1',2'), 4.98(dd, 1H, H-3'), 4.49(bs, 2H, NH₂), 4.13(m, 3H, H-4',5',5''), 1.11(m, 28H, TIPDS)

(3) Synthesis of 5-amino-1-(2-deoxy-3,5-O-TIPDS-β-D-ribofuranosyl)imidazole-4-carbonitrile To a suspension of 1.28 g (2.16 mmol) of the compound obtained in (2) and 50mg of 2,2'-azobis-(isobutyronitrile) (AIBN) in 20 ml of toluene was added 0.87 ml (1.5 equivalents) of tributyltin hydride (nBu₃SnH). The mixture was heated under reflux at 120° C. for 40 minutes under argon stream, and the solvent was evaporated. The residue was adsorbed onto a silica gel column (2.7×5 cm), eluted with an n-hexane-ethyl acetate (3:1 to 1:1) solvent mixture, and crystallized from n-hexane to obtain 1.0 g of the desired compound in crystal form (yield: 99%).

m.p.: 95°–96° C.

Elemental analysis (for $C_{21}H_{38}N_4O_4Si_2$): Calcd. C 54.04%, H 8.21%, N 12.00%, Found C 54.15%, H 8.31%, N 11.86%.

MS(m/z): 466 (M⁺)

¹H-NMR(CDCl₃): 7.09(s, 1H, H-2), 5.82(dd, 1H, H-1', J1',2'=5.38, J1',2''=5.61), 4.75(m, 1H, H-3'), 4.40(bs, 2H, NH₃), 3.97(m, 2H, H-5',5''), 3.82(m, 1H, H-4'), 2.52(m, 2H, H-2',2''), 1.06(m, 28H, TIPDS)

EXAMPLE E1

Synthesis of 5-iodo-1-(2-deoxy-3,5-0-TIPDS-β-D-ribofuranosyl)imidazole-4-carbonitrile [Formula [IIg]: X=iodine, $R^3$(2'-position)=hydrogen atom, $R^3$(5'-position)=OR², $R^2$=TIPDS (over 3'-position and 5'-position)]

The procedure of Example B1 was followed with 500 mg (1.07 mmol) of the compound obtained in Reference Example E1(3), 6 ml of diiodomethane, and 0.6 ml of isoamyl nitrite. The product was recrystallized from n-hexane to obtain 397 mg of the desired compound in crystal form (yield: 64.3%).

m.p.: 148°–149° C.

Elemental analysis (for $C_{21}H_{36}N_3O_4ISi_2$): Calcd. C 43.67%, H 6.28%, N 7.27%, Found C 43.27%, H 6.35%, N 7.33%.

MS(m/z): 577 (M⁺)

¹H-NMR(CDCl₃) 8.06(s, 1H, H-2), 5.89(dd, 1H, H-1', J1',2'=6.84, J1',2''=1.95), 4.59(ddd, 1H, H-3', J3',2'=7.56, J3',2''=2.20, J3',4'=8.06), 4.08(m, 2H, H-5',5''), 3.84(dt, 1H, H-4', J4',3'=8.06, J4',5'=2.93), 2.48(m, 2H, H-2',2''), 1.05(m, 28H, TIPDS)

EXAMPLE E2

(1) Synthesis of 5-(2-trimethylsilyl-1-ethyn-1-yl)-1-(2-deoxy-3,5-O-TIPDS-β-D-ribofuranosyl)imidazole-4-carbonitrile The procedure of Examples B2 - B5 was followed (the reaction being carried out at 100° C. for 2 hours) with 577 mg (1 mmol) of the compound obtained in Example E1, 18 mg (5 mol%) of bis(benzonitrile)palladium dichloride, and 0.17 ml (1.2 mmol) of trimethylsilylacetylene. The product was recrystallized from n-hexane to obtain 322 mg of yellow crystals of the desired compound (yield: 58.9%).

m.p.: 128°–129° C.

Elemental analysis (for $C_{26}H_{45}N_3O_4Si_3$) Calcd. C 56.99%, H 8.28%, N 7.67%, Found C 56.77%, H 8.45%, N 7.70%

MS(m/z): 547 (M⁺)

¹H-NMR(CDCl₃) 7.85(s, 1H, H-2), 600(dd, 1H, H-1', J1',2'=6.35, J1',2''=2.44), 4.56(ddd, 1H, H-3 ), 4.06(m, 2H, H-5',5''), 3.84 dt, 1H, H-4 ), 2.50(m, 2H, H-2',2''), 1.04(m, 78H, TIPDS), 0 29(s, 9H, TMS)

(2) Synthesis of 5-ethynyl-1-(2-deoxy-β-D-ribofuranosyl)imidazole-4-carbonitrile [Formula [I]: A=CN-, $R^1$=hydrogen atom, R=2-deoxy-D-ribose]

To a solution of 164 mg (0.3 mmol) of the compound obtained in (1) in 5 ml of tetrahydrofuran (THF) was added 0.99 ml (3.3 equivalents) of tetrabutylammonium fluoride (1M in THF) under ice-cooled conditions, and the mixture was stirred at room temperature for 10 minutes After the reaction, the solvent was evaporated while the residue was adsorbed onto a silica gel column (1.8×6 cm) and eluted with a 5–15% ethanol-chloroform solvent mixture, whereafter the solvent was evaporated to obtain 73 mg of the desired compound as a glutinous substance (yield: 97%).

MS(m/z) 233 (M⁺)

¹H-NMR(DMSO-d6): 8.29(s, 1H, H-2), 6.08(dd, 1H, H-1', J1',2'=6.35, J1',2''=6.59), 5.37(s, 1H, ≡CH), 5.36(d, 1H, 3'-OH, J3'-OH,3'=4.39), 4.97(t, 1H, 5'-OH, J5'-OH,5'=5.25), 4.29(m, 1H, H-3 ) 3.86(m, 1H, H-4'), 3.53(m, 2H, H-5',5''), 3.30(m, 2H, H-2')

EXAMPLE E3

Synthesis of 5-ethynyl-1-(2-deoxy-β-D-ribofuranosyl)imidazole-4-carboxamide (Formula [I]: A=CONH-2, $R^1$=hydrogen atom, R=2-deoxy-D-ribose]

To a solution of the compound obtained in Example E2(2) in 3 ml of an aqueous ammonia-methanol (1 1) solvent mixture was added 0.1 ml of hydrogen peroxide, and the resulting solution was stirred at room temperature for 30 minutes. After the reaction, the solvent was evaporated while the residue was adsorbed onto a silica gel column (1.8×10 cm), eluted with a 5–15% ethanol-chloroform solvent mixture, and crystallized from an ethanol-hexane solvent mixture to obtain 44 mg of the desired compound in crystal form (yield:56.0%)

m.p.: 174°–175° C.

Elemental analysis (for $C_{11}H_{13}N_3O_4$): Calcd. C 52.59%, H 5.21%, N 16.73%; Found C 52.49%, H 5.17%, N 16.59%.

MS(m/z): 251 (M⁺)

¹H-NMR(DMSO-d6): 8.09(s, 1H, H-2), 7.34, 7.24(each bs, 2H, CONH₂), 6.08(t, 1H, H-1', J1',2'=J1',2''=6.6), 5.33(d, 1H, 3'-OH, J3'OH,3'=4.15), 4.96(t, 1H, 5'-OH, J5'-OH,5'=5.37), 4.87(s, 1H, ≡CH), 4.33(m, 1H, H-3'), 3.84(m, 1H, H-4'), 3.31(m, 2H, H-5',5''), 2.40(m, 2H, H-2')

EXAMPLE E4

Synthesis of 5-iodo-1-(5l-deoxy-2,3-isopropylidene-β-D-ribofuranosyl)imidazole-4-carbonitrile [Formula [IIg]: X=iodine, $R^3$(2'-position)=OR², $R^3$(5'-position)=hydrogen atom, $R^2$=isopropylidene (over 2'-position and 3'-position)]

The procedure of Example B1 was followed with 1.056 g (4 mmol) of 5-amino-1-(5l-deoxy-2,3-isopropylidene-β-D-ribofuranosyl)imidazole-4-carbonitrile (J. Med. Chem., 18, 1237 (1975)), 20 ml of diiodomethane, and 2 ml of isoamyl nitrite to obtain 982 mg of the desired compound as a glutinous substance (yield: 65.5%).

MS(m/z): 375 (M⁺)

$^1$H-NMR(CDCl$_3$): 7.79(s, 1H, H-2), 5.75 (d, 1H, H-1', J1'=2.93), 4.83(dd, 1H, H-2', J2',1'=2.93, 1 J2',3'=6.34), 4.54(dd, 1H, H-3', J3',2'=6.34, J3',4'=3.90), 4.35(dd, 1H, H-4', J4',3'=3.90, J4',5'=6.60), 1.62, 1.37(each s, 6H, isopropylidene), 1.43(d, 3H, H-5', J5',4'=6.60)

EXAMPLE E5

(1) Synthesis of 5-(2-trimethylsilyl-1-ethyn-1-yl)-1-(5-deoxy-2,3-isopropylidene-β-D-ribofuranoxyl)imidazole-4-carbonitrile The procedure of Examples B2–B5 was followed (the reaction being carried out at 100° C. for 5.5 hours) with 739 mg (1.97 mmol) of the compound obtained in Example E4, 36 mg (5 mol %) of bis(benzonitrile)palladium dichloride, and 0.34 ml (1.2 equivalents) of trimethylsilylacetylene. The product was recrystallized from n-hexane to obtain 278 mg of the desired compound (yield: 40.9%).

m.p.: 70°–72° C.

Elemental analysis (for C$_{17}$H$_{23}$N$_3$O$_3$Si): Calcd. C 59.10%, H .671%, N 12.16%; Found C 58.94%, H 6.79%, N 12.14%.

MS(m/z): 345(M$^+$)

$^1$H-NMR(CDCl$_3$): 7.61(s, 1H, H-2), 5.80(d, 1H, H-1', J1',2'=2.45), 4.99(dd, 1H, H-2', J2',1'=2.45, J2',3'=6.11), 4.42(m, 2H, H-3',4'), 1.58, 1.35(each s, 6H, isopropylidene), 1.40(d, 3H, H-5')

(2l) Synthesis of 5-(2-trimethylsilyl-1-ethyn-1-yl)-1-(5-deoxy-β-D-ribofuranosyl)imidazole-4-carbonitrile A solution of 50 mg (0.14 mmol) of the compound obtained in (1) in 3 ml of a 90% aqueous solution of trifluoroacetic acid (TFA) was stirred at room temperature for 10 minutes. After the reaction, the solvent was evaporated and the residue was subjected to azeotropic distillation three times with ethanol. The resultant residue was adsorbed onto a silica gel column (1.8×7 cm) and eluted with a 0–4% ethanol-chloroform solvent mixture, whereafter the solvent was evaporated to obtain 43 mg of the desired compound as a glutinous substance (yield: 97.3%).

MS(m/z): 305(M$^+$)

$^1$H-NMR(DMSO-d6+D$_2$O): 8.26(s, 1H, H-2), 5.61(d, 1H, H-1', J1',2'=4.88), 4.39(dd, 1H, H-2', J2',2'=4.88, J2',3'=5.13), 3.90(m, 2H, H-3',4'), 1.30(d, 3H, H-5', J5',4'=7.35), 0.28(s, 9H, TMS)

(3) Synthesis of 5-ethynyl-1-(5l-deoxy-β-D-ribofuranosyl)imidazole-4-carbonitrile [Formula [I]: A=CN, R$^1$=hydrogen atom, R=5-deoxy-D-ribose]

To 36 mg (0.12 mmol) of the compound obtained in (2) was added 3 ml of methanolic ammonia, and the mixture was left standing overnight to cause reaction After the reaction, the solvent was evaporated while the residue was adsorbed onto a silica gel column (1.8×5 cm) and eluted with a 0–6% ethanol-chloroform solvent mixture, whereafter the solvent was evaporated to obtain 18 mg of the desired compound (yield: 65.5%)

MS(m/z) 233(M$^+$)

1H-NMR(DMSO-d6) 8.26(s, 1H, H-2), 5.60(d, 1H, H-1', J1',2'=5.13), 5.58(d, 1, 2'-OH, J2'-OH,2'=5.86), 5 35(s, 1H, ≡CH), 5.24(d, 1H, 3'-OH, J3'-OH,3'=5.13), 4.38(m, 1H, H-2'), 3.87(m, 2H, H-3', 4'), 1.27(d, 3H, H-5', J5',4'=6.35)

EXAMPLE E6

Synthesis of 5-ethynyl-1-(5-deoxy-β-D-ribofuranosyl)imidazole-4-carboxamide [Formula [I]A=CONH-2, R$^1$=hydrogen atom, R=5-deoxy-D-ribose]

To a solution of 84 mg (0.28 mmol) of the compound obtained in Example E5(2) in 3 ml of aqueous ammoniamethanol (1:1) was added 0.1 ml of hydrogen peroxide, and the resulting solution was stirred at room temperature for 30 minutes to cause reaction. After the reaction, the solvent was evaporated while the residue was adsorbed onto a silica gel column (1.8×8 cm), eluted with 5–15% ethanol-chloroform, and recrystallized from an ethanolhexane solvent mixture to obtain 47 mg of the desired compound as white crystals (yield: 68%)

m.p.: 171°–172° C.

Elemental analysis (for C$_{11}$H$_{13}$N$_3$O$_4$) Calcd. C 52.58%, H 5.22%, N 16 73%, Found C 52.49%, H 5.28%, N 16.67%.

MS(m/z) 251(M$^+$)

$^1$H-NMR(DMSO-d6): 8.05(s, 1H, H-2), 7.35, 7.25(each bs, 2H, CONH$_2$), 5.62(d, 1H, H-1', J1',2'=5.13), 5.52(d, 1H, 2'-OH), 5.21(d, 1H, 3'-OH), 4.86(s, 1H, ≡CH), 4.39(m, 1H, H-2'), 3.87(m, 2H, H-3',4'), 1.29(d, 3H, H-5', J5',4'=6.1)

EXAMPLE E7

(1) Synthesis of 5-ethynyl-1-(5-deoxy-2,3-isopropylidene-β-D-ribofuranosyl)imidazole-4-carbonitrile To a solution of 278 mg (0.81 mmol) of the compound obtained in Example E5(1) in 5 ml of tetrahydrofuran was added 1.2 ml (1.5 equivalents) of tetrabutylammonium fluoride under ice-cooled conditions, and the mixture was stirred at room temperature for 10 minutes to cause reaction. After the reaction, the solvent was evaporated while the residue was adsorbed onto a silica gel column (1.8×10 cm) and eluted with hexane-ethyl acetate (2:1), whereafter the solvent was evaporated to obtain 198 mg of the desired compound (yield: 89.5%).

(2) Synthesis of 5-ethynyl-1-(5-deoxy-β-D-ribofuranosyl)imidazole-4-carbonitrile [Formula [I]: A=CN, R$^1$=hydrogen atom, R=5-deoxy-D-ribose]

A solution of 198 mg (0.73 mmol) of the compound obtained in (1) in 10 ml of a 90% aqueous solution of TFA was stirred at room temperature for 10 minutes to cause reaction. After the reaction, the solvent was evaporated and the residue was purified similarly as in Example E5(3) to obtain 164 mg of the desired compound (yield: 97%).

EXAMPLE F

Synthesis of 5-ethynyl-1-β-D-ribofuranosylimidazole-4-carboxamide 5'-phosphate [Formula[I]]A=CONH$_2$, R$^1$=hydrogen atom, R=5-phosphoryl-D-ribose]

To an ice cooled solution of 2.67 g of in 60 ml of trimethylphosphoric acid is added dropwise 1 53 g of phosphorus oxychloride, and the mixture stirred for 1 hour. The reaction solution is poured into 100 ml of ice-cooled water containing 8 g of sodium hydrogencarbonate, and the mixture stirred for 1 hour. Then 100 ml of ether is added, and the resulting solution partitioned. The aqueous layer is concentrated, adsorbed onto an anion exchange resin, Dowex 1 (formic acid type), and eluted with 1 M formic acid solution. Fractions containing the desired compound are combined, concentrated, and freeze-dried to obtain 5-ethynyl-1-β-D-ribofuranosylimidazole-4-carboxamide 5'-phosphate.

We claim:

1. An imidazole derivative represented by the formula:

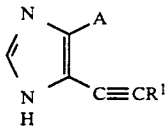
[Ib]

wherein A is $CONH_2$ or CN; and $R^1$ is a hydrogen atom, lower alkyl, hydroxy lower alkyl, or phenyl.

2. A pharmaceutical composition for the treatment of tumors which comprises as an active ingredient, a pharmaceutically effective amount of an imidazole derivative represented by the formula:

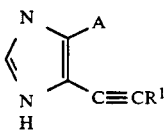

wherein A is $CONH_2$ or CN; and $R^1$ is a hydrogen atom, lower alkyl, hydroxy lower alkyl, or phenyl.

* * * * *